United States Patent
Bonnet et al.

(10) Patent No.: US 10,155,049 B2
(45) Date of Patent: *Dec. 18, 2018

(54) INFLUENZA ANTIGEN DELIVERY VECTORS AND CONSTRUCTS

(71) Applicant: ALTIMMUNE UK LIMITED, London (GB)

(72) Inventors: Dominique Bonnet, Geispolsheim (FR); Carlton B. Brown, Santa Cruz la Laguna (GT); Bertrand V. Georges, London (GB); Philip J. Sizer, Helsby (GB)

(73) Assignee: Altimmune UK, LTD, London (GB)

( * ) Notice: Subject to any disclaimer, the term of this patent is extended or adjusted under 35 U.S.C. 154(b) by 237 days.

This patent is subject to a terminal disclaimer.

(21) Appl. No.: 15/242,682

(22) Filed: Aug. 22, 2016

(65) Prior Publication Data
US 2017/0049898 A1  Feb. 23, 2017

Related U.S. Application Data

(63) Continuation of application No. 14/139,293, filed on Dec. 23, 2013, now Pat. No. 9,446,143, which is a (Continued)

(30) Foreign Application Priority Data

Aug. 31, 2007  (GB) .................................. 0716992.3

(51) Int. Cl.
*A61K 39/12* (2006.01)
*A61K 47/58* (2017.01)
(Continued)

(52) U.S. Cl.
CPC .............. *A61K 47/58* (2017.08); *A61K 39/12* (2013.01); *A61K 39/145* (2013.01); *A61K 39/21* (2013.01);
(Continued)

(58) Field of Classification Search
CPC .. A61K 2039/60; A61K 39/12; A61K 39/385; A61K 2039/6031; A61K 47/4833;
(Continued)

(56) References Cited

U.S. PATENT DOCUMENTS 3,065,141 A   11/1962  Gessler et al.
3,843,443 A   10/1974  Fishman
(Continued)

FOREIGN PATENT DOCUMENTS

CA    2070254     12/1993
EP    0 327 070   8/1989
(Continued)

OTHER PUBLICATIONS

"Solvent Systems and Their Selection in Pharmaceutics and Biopharmaceutics," Springer (2007) Augustijns, P. and Brewster, M., eds. "Chapter I. Principles of Solubility," Gong et al., pp. 1-27.
(Continued)

*Primary Examiner* — Randall L Beane
(74) *Attorney, Agent, or Firm* — Koren Anderson

(57) ABSTRACT

The present invention relates to fluorocarbon vectors for the delivery of influenza antigens to immunoresponsive target cells. It further relates to fluorocarbon vector-influenza antigen constructs and the use of such vectors associated with antigens as vaccines and immunotherapeutics in animals, including humans.

15 Claims, 7 Drawing Sheets

Figure 1:
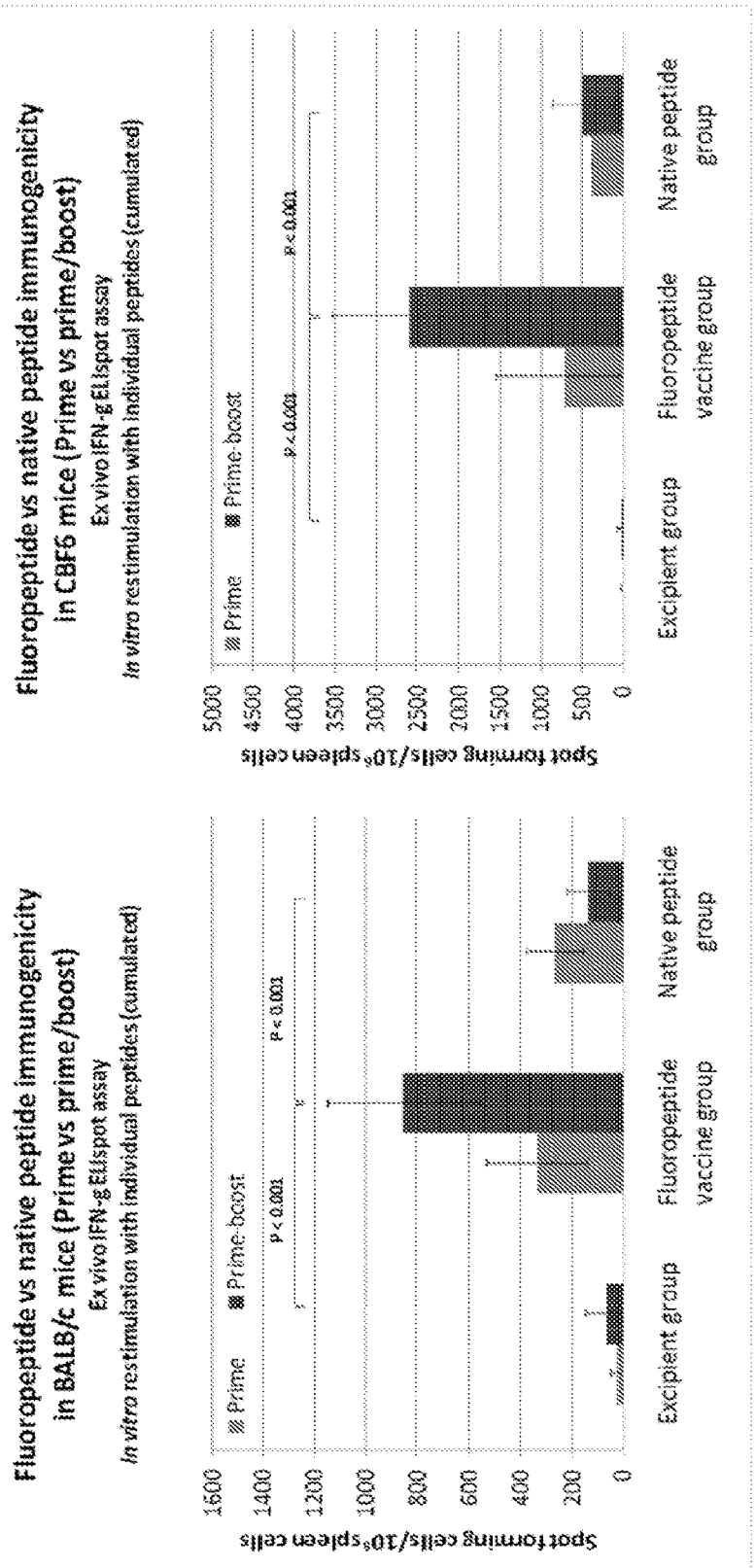

Specification includes a Sequence Listing.

Related U.S. Application Data continuation of application No. 12/201,894, filed on Aug. 29, 2008, now Pat. No. 8,642,531.

(60) Provisional application No. 60/969,481, filed on Aug. 31, 2007.

(51) Int. Cl.

| | | |
|---|---|---|
| A61K 39/145 | (2006.01) | |
| A61K 39/21 | (2006.01) | |
| A61K 39/385 | (2006.01) | |
| C07K 14/005 | (2006.01) | |
| A61K 47/54 | (2017.01) | |
| A61K 47/64 | (2017.01) | |
| A61K 39/00 | (2006.01) | |

(52) U.S. Cl.
CPC ............ *A61K 39/385* (2013.01); *A61K 47/54* (2017.08); *A61K 47/646* (2017.08); *C07K 14/005* (2013.01); *A61K 2039/54* (2013.01); *A61K 2039/55511* (2013.01); *A61K 2039/60* (2013.01); *A61K 2039/6018* (2013.01); *A61K 2039/6031* (2013.01); *C12N 2740/16122* (2013.01); *C12N 2740/16134* (2013.01); *C12N 2760/16034* (2013.01); *C12N 2760/16122* (2013.01); *C12N 2760/16222* (2013.01); *C12N 2760/16322* (2013.01)

(58) Field of Classification Search
CPC .................. C07K 14/005; C07K 2/00; C12N 2740/16134; C12N 2740/16034; C12N 2760/16034; C07C 19/08
See application file for complete search history.

(56) References Cited

U.S. PATENT DOCUMENTS

| | | | |
|---|---|---|---|
| 4,332,787 A | 6/1982 | Homcy et al. | |
| 4,689,398 A | 8/1987 | Wu et al. | |
| 4,954,444 A | 9/1990 | Eveleigh et al. | |
| 5,021,551 A | 6/1991 | Allen et al. | |
| 5,055,562 A | 10/1991 | Koganty et al. | |
| 5,401,634 A | 3/1995 | Milbrath | |
| 5,635,181 A | 6/1997 | Harwood et al. | |
| 5,728,578 A | 3/1998 | Jahn et al. | |
| 5,817,318 A | 10/1998 | Sia et al. | |
| 5,858,374 A | 1/1999 | Levy | |
| 5,871,746 A | 2/1999 | Boutillon et al. | |
| 5,919,459 A | 7/1999 | Nacy et al. | |
| 6,069,232 A | 5/2000 | Malikayl et al. | |
| 6,121,123 A | 9/2000 | Lyons et al. | |
| 6,174,532 B1 | 1/2001 | Campo et al. | |
| 6,270,778 B1 | 8/2001 | Kawakami et al. | |
| 6,413,516 B1 | 7/2002 | Chang et al. | |
| 6,491,926 B1 | 12/2002 | Morton | |
| 6,537,560 B1 | 3/2003 | Kawakami et al. | |
| 6,541,009 B1 | 4/2003 | Inglis et al. | |
| 6,548,046 B1 | 4/2003 | Lanza et al. | |
| 6,676,963 B1 | 1/2004 | Lanza et al. | |
| 6,710,035 B2 | 3/2004 | Felgner et al. | |
| 6,884,414 B1 | 4/2005 | Palese et al. | |
| 7,687,455 B2 | 3/2010 | Bonnet et al. | |
| 8,110,540 B2 | 2/2012 | Bonnet et al. | |
| 8,110,541 B2 | 2/2012 | Bonnet et al. | |
| 8,129,333 B2 | 3/2012 | Bonnet et al. | |
| 8,642,531 B2 * | 2/2014 | Bonnet ................ | A61K 39/145 514/1.1 |
| 9,446,143 B2 * | 9/2016 | Bonnet ................ | A61K 39/145 |
| 2005/0009008 A1 | 1/2005 | Robinson et al. | |
| 2006/0013820 A1 | 1/2006 | Bonnet et al. | |
| 2007/0172929 A1 | 7/2007 | Maassab et al. | |
| 2008/0145383 A1 | 6/2008 | Zauner et al. | |
| 2009/0023895 A1 | 1/2009 | Miyakawa et al. | |
| 2010/0047275 A1 | 2/2010 | Stoloff et al. | |
| 2012/0315293 A1 | 12/2012 | Bonnet et al. | |
| 2013/0330382 A1 | 12/2013 | Brown et al. | |

FOREIGN PATENT DOCUMENTS

| | | | |
|---|---|---|---|
| EP | 2190474 | 6/2010 | |
| EP | 1991563 | 11/2011 | |
| EP | 2383284 | 11/2011 | |
| EP | 2383285 | 11/2011 | |
| FR | 2752161 | 2/1998 | |
| FR | 2883563 | 9/2006 | |
| GB | 1193378 | 5/1970 | |
| GB | 2465733 | 12/2010 | |
| RU | 2218175 | 12/2003 | |
| WO | 1994/026903 | 11/1994 | |
| WO | 99/21541 | 5/1996 | |
| WO | 99/45954 | 9/1999 | |
| WO | 2001/00225 | 1/2001 | |
| WO | 2001/70772 | 9/2001 | |
| WO | 2002/072627 | 9/2002 | |
| WO | 03/040165 | 5/2003 | |
| WO | 2004/031211 | 4/2004 | |
| WO | 05/099752 | 10/2005 | |
| WO | 2005/094891 | 10/2005 | |
| WO | WO-2005099752 A2 * | 10/2005 | ............ A61K 39/21 |
| WO | 2005/120564 | 12/2005 | |
| WO | 2006/074024 | 6/2006 | |
| WO | 2007/085969 | 8/2007 | |
| WO | 2007/091030 | 8/2007 | |
| WO | 2009/027688 | 3/2009 | |
| WO | 2012/090002 | 7/2012 | |

OTHER PUBLICATIONS

NP_775530.1 polymerase PB1 [Influenza A virus (A/Puerto Rico/8/34/Mount Sinai(H1N1))], NCBI.NLM.gov (Aug. 31, 2005), also available at http://www.ncbi.nlm.gov/protein/NP_775530.1?report=genpet (last visited Aug. 12, 2015).

Cox et al. (2004) "Influenza Virus: Immunity and Vaccination Strategies. Comparison of the Immune Response to Inactivated and Live, Attenuated Influenza Vaccines" Scandinavian Journal of Immunology, 59:1-15.

Bijker, et al. (2007) "CD8+ CTL Priming by Exact Peptide Epitopes in Incomplete Freund's Adjuvant Induces a Vanishing CTL Response, whereas Long Peptides Induce Sustained CTL Reactivity" J. Immunol., 179: 5033-5040.

Nijman et al. ( 1993) "Identification of peptide sequences that potentially trigger HLA-A2.1-restricted cytotoxic T lymohocytes," Eur. J. Immunol. 23:1215-1219.

Notice of Opposition and Statement of Facts and Arguments in Support of Opposition filed on Aug. 23, 2012 in EP Patent No. 1991563 owned by PepTcell Limited (corresponds to PepTcell's PCT/GB2007/000383) (31 pages).

Odorico et al. (2003) "BEPITOPE: predicting the location of continuous epitopes and patterns in proteins," J. Mol. Recognit. 16(1):20-2.

Opposition statement against related Chilean Application No. 2559-2008 by Associacion Nacional de Laboratorios Farmaceuticos AS (in Spanish), and its English translation (7 pages).

Panina-Bordignon et al. (1989) "Universally immunogenic T cell epitopes: promiscuous binding to human MHC class II and promiscuous recognition by T cells," Eur. J. Immunol. 19:2237-2242.

Parker et al. (1992) "Sequence Motifs important for Peptide Binding to the Human MHC Class I Molecule, HLA-A2" J. Immunol. 149(11):3580-3587.

Partial International Search Report and Invitation to Pay Additional Fees for PCT/GB2005/001279, dated Sep. 7, 2005 (7 pages).

Pellequer et al. (1993) "PREDITOP: A program for antigenicity prediction," J. Mol. Graph. 11(3):204-10.

Plotnicky et al. (2003) "The immunodominant influenza matrix T cell epitope recognized in human induces influenza protection in HLA-A2/Kb transgenic mice," Virology 309:320-329.

(56) References Cited

OTHER PUBLICATIONS

Rammensee (1995) "Chemistry of Peptides Associated with MHC Class I and Class II Molecules," Current Opinion in Immunology 7:85-96.
Rammensee et al. (1999) "SYFPEITHI: database for MHC ligands and peptide motifs," Immunogenetics 50:213-219.
Reichel, et al. (1999) "Stereochemical Dependence of the Self-Assembly of the Imunoadjuvants Pam3Cys-Ser and Pam3Cys-Ser," J. Am. Chem. Soc 121: 79S9-97.
Reyes et al. (1991) "Binding of Radioiodinated Influenza Virus Peptides to Class I MHC Molecules and to other Cellular Proteins as Analyzed by Gel Filtration and Photoaffinity Labeling," Mol. Immunol. 28(4-5):341-348.
Riess et al. (1991) "Highly Effective Surfactants with Low Hemolytic Activity," Adv. Mater. 3(5):249-51.
Rosenberg et al. (1997) "Vigorous HIV-1-specific CD4+ T cell responses associated with control of viremia," Science 278:1447-50.
Scheibenbogen et al. (1997) "A Sensitive ELISPOT Assay for Detection of CD8+ T Lymphocytes Specific for HLA Class I-binding Peptide Epitopes Derived from Influenza Proteins in the Blood of Healthy Donors and Melanoma Patients," Clin. Cancer Res. 3:221-226.
Schlaphoff et al. (2007) "Functional and Phenotypic Characterization of Peptide-Vaccine-Induced HGV-specific CD8+ T Cells in Healthy Individuals and Chronic Hepatitis C Patients," Vaccine 25 (37-38): 6793-6806.
Schmittel et al. (2001) "Application of the IFN-γ ELISPOT assay to quantify T cell responses against proteins," J. Immunol. Methods 247:17-24.
Sette et al. (1998) "HLA supertypes and supermotifs: a functional perspective on HLA polymorphism," Current Opinion in Immunology 10:478-482.
Speiser et al. (2005) "Rapid and strong human CD8+ T cell responses to vaccination with peptide, IFA, and CpG oligodeoxynucleotide 7909," The Journal of Clinical Investigation 115(3):739-746.
Sugimoto et al. (1993) "Peptide Vaccine," Cell Technology 12(1):58-63, 74. Original article in Japanese with English translation attached (20 pages).
Takeshita (1995) "Molecular Analysis of the Same HIV Peptide Functionally Binding to Both a Class I and a Class II MHC Molecule," J. Immunol. 154:1973-86.
Tang et al. (2005) "Isolation and Characterization of H3N2 Influenza A Virus from Turkeys," Avian Diseases 49:207-213.
Taubenberger et al. (1997) "Initial Genetic Characterization of the 1918 "Spanish" Influenza Virus," Science 275:1793-1796.
Thimme et al. (2001) "Determinants of viral clearance and persistence during acute hepatitis C virus infection," J. Exp. Med. 11:1395-1406.
Third Party Observations against EP07712678.7 owned by PepTcell Limited (EP Patent No. 1991563, corresponds to PepTcell's PCT/GB2007/000383) filed on Dec. 17, 2008 with European Patent Office (13 pages).
Thomas et al. (2006) "Cell-Mediated Protection in Influenza Infection," Emerg. Infect. Dis. 12(1):48-54.
Thust et al. (2003) "Protease-catalyzed peptide synthesis for the site-specific incorporation of alpha-fluoroalkyl amino acids into peptides," J Organic Chem 68(6):2290-2296.
Voeten et al. (2001) "Antigen processing for MHC class I restricted presentation of exogenous influenza A virus nucleoprotein by B-lymphoblastoid cells," Clin. Exp. Immunol. 125:423-431.
Wang et al. (2007) "CTL epitopes for influenza A including the H5N1 bird flu; genome-,pathoqen-, and HLA-wide screening," Vaccine 25(15):2823-2831.
Written Opinion of the International Searching Authority for PCT/GB2007/000383 (PepTcell Limited), dated Aug. 7, 2008 (10 pages).
Written Opinion of the International Searching Authority, International Application No. PCT/GB2008/002930 (Immune Targeting Systems), dated Feb. 28, 2010 (5 pages).
Yang et al. (2005) "Expression of HLA-DP0401 Molecules for Identification of DP0401 Restricted Antigen Specific T Cells," J. Clin. Immunol. 25(5):428-436.
Yang et al. (2006) "Multiplex mapping of CD4 T cell epitopes using class II tetramers," Clinical Immunology 120:21-32.
Zhong et al. (2003) "Genome-wide Characterization of a Viral Cytotoxic T Lymphocyte Epitope Repertoire," J. Biol. Chem. 278(46):45135-45144.
Beebe et al. (2008) "Formulation and characterization of a ten-peptide single vial vaccine, EP-2101, designed to induce cytotoxic T-lymphocyte responses for cancer immunotherapy" Human Vaccines, 4(3):210-218.
Bonnet et al. (2005) "Effect of Glycoamphiphiles on the Solubilization and Dendritic Cell Uptake of a Lipopeptide: A Preliminary Study" Mol. Pharm., 2(5):420-427.
Database Uniprot Nov. 1, 1996 (Nov. 1, 1996), Castrucci M et al.: "Genetic reassortment between avian and human influenza A virus" XP002442455 accession No. Q67194.
Deckert, C.A. (1980) "Pattern Etching of CVD S13N4/S102 Composites in HF/Glycerol Mixtures," Journal of the Electrochemical Society 127(2):2433-2438.
Deres et al. (1989) "In vivo priming of virus-specific cytotoxic T lymphocytes with synthetic lipopeptide vaccine" Nature, 342:561-564.
Do et al. (2008) "Broad T cell immunity to the LcrV virulence protein is induced by targeted delivery to DEC-205/CD205-positive mouse dendritic cells" Eur. J. Immunol., 38:20-29.
Europharmatoday website (http://www.europharmatoday.com/2009/08/startup-profile-immunetargeting-systems-ltd-synthetic-vaccines-against-mutating-viruses.html, accessed May 11, 2011).
Fayolle et al. (2004) "Bordetella pertussis adenylate cyclase delivers chemically coupled CD8+T-cell epitopes to dendritic cells and elicits CTL in vivo" Vaccine, 23:604-614.
Felix et al. (1995) "Pegylated peptides. IV. Enhanced biological activity of site-directed pegylated GRF analogs" Int. J. Pept. Protein Res., 46:253-264.
International Search Report for PCT/GB11/001781 (Immune Targeting Systems), dated Apr. 10, 2012 (4 pages).
Jones et al. (2005) "Characterisation of cell-penetrating peptide-mediated peptide delivery" Br. J. Pharmacol., 145:1093-1102.
Krafft et al. (2009) "Chemistry, Physical Chemistry, and Uses of Molecular Fluorocarbon-Hydrocarbon Diblocks, Triblocks, and Related Compounds—Unique "Apolar" Components for Self-Assembled Colloid and Interface Engineering" Chem. Rev., 109:1714-1792.
Ozer et al. ( 1999) "Synthesis of perfluoroalkyltated beta-alanine and some peptide derivatives: an access to original surfactants" Amino Acids, 16:381-389.
Perrie et al.(2007) "Recent developments in particulate-based vaccines" Recent Pat. Drug Deliv. Formul.,1(2):117-129.
Samad et al. (2007) "Liposomal drug delivery systems: an update review" Current Drug Deliv.,4:297-305.
Alatrakchi et al. (2002) "Strong CD4 Th1 responses to HIV and hepatitis C virus in HIV-infected long-term non-progressors co-infected with hepatitis C virus," AIDS 16(5):713-7.
Alexander et al. (1997) "Derivation of HLA-A11/Kb Transgenic Mice: Functional CTL Repertoire and Recognition of Human A11-Restricted CTL Epitopes," J. Immunol. 159(10):4753-61.
Alix (1999) "Predictive estimation of protein linear epitopes by using the program PEOPLE," Vaccine 18(3-4):311-4.
Bastin et al. (1987) "Use of Synthetic Peptides of Influenza Nucleoprotein to define epitopes recognized by Class I-restricted Cytotoxic T Lymphocytes" J. Exp. Med. 165:1508-1523.
BenMohamed et al. (2003) "Identification of novel immunodominant CD4+ Th1-type T-cell peptide epitopes from herpes simplex virus glycoprotein D that confer protective immunity," Journal of Virology 77(17):9463-9473.
Berkhoff et al. (2005) "Functional Constraints of Influenza A Virus Epitopes Limit Escape from Cytotoxic T Lymohocytes," J. Virol. 79(17):11239-11246.
Boaz et al. (2002) "Presence of HIV-1 Gag-specific IFN-gamma+ IL-2+ and CD28+IL-2+ CD4 T cell responses is associated with nonprogression in HIV-1 infection," The Journal of Immunology 169:6376-85.

(56) References Cited

OTHER PUBLICATIONS

Bodmer et al. (1989) "Class I cross-restricted T cells reveal low responder allele due to processing of viral antigen," Nature 337:653-655.
Boon et al. (2005) "Functional profile of human influenza virus-specific cytotoxic T lymphocyte activity is influenced by interleukin-2 concentration and epitope specificity," Clin. Exp. Immunol. 142:45-52.
Cheuk et al. (2005) "Strong memory CD8+ T cell responses against immunodominant and three new subdominant HLA-B27-restricted influenza A CTL epitopes following secondary infection of HLA-B27 transgenic mice," Cellular Immunology 234:110-123.
Crowe et al. (2006) "Identification of protective and non-protective T cell epitopes in influenza," Vaccine 24:452-456.
Database WPI Week 200416; Thomson Scientific, London, GB; AN 2004-165290; XP002508268 (2 Pages).
De Groot et al. (1997) "An Interactive Web Site Providing Major Histocompatibility Ligand Predictions: Applications to HIV Research," AIDS Res. and Human Retroviruses 13(7):529-531.
Deliyannis et al. (2002) "Induction of Long-Term Memory CD8+ T Cells for Recall of Viral Clearing Responses against Influenza Virus," Journal of Virology 76(9):4212-4221.
Doolan et al. (2000) "HLA-DR-Promiscuous T Cell Epitopes from Plasmodium falciparum Pre-Erythrocytic-Stage Antigens Restricted by Multiple HLA Class II Alleles," J. Immunol.165: 1123-1137.
English Translation and Original Search Report dated Feb. 8, 2012 for Taiwanese Patent Application No. 097133417 (Taiwanese counterpart of WO-05099752, Immune Targeting Systems, 2 pages).
EP Search Report for Application No. EP 05 72 9595 dated Jan. 26, 2009 (5 pages).
Faroux-Corlay et al. (2000) "Synthesis of single- and double-chain fluorocarbon and hydrocarbon galactosyl amphiphiles and their anti-HIV-1 activity," Carbohydrate Res., 327:223-60.
Filippov et al. (2002) "Use of benzloxycarbonyl (Z)-based fluorophillic taging reagents in the purification of synthetic peptide," Tel. Let., 43:7809-12.
Frahm et al. (2007) "Extensive HLA class I allele promiscuity among viral CTL epitopes," Eur. J. Immunol. 37:2419-2433.
Gahery-Segard et al. (2000) "Multiepitopic B- and T-Cell Responses Induced in Humans by a Human Immunodeficiency Virus Type 1 Lipopeptide Vaccine," Journal of Virology 74(4):1694-1703.
Gahery-Segard et al. (2003) "Long-Term Specific Immune Responses Induced in Humans by a Human Immunodeficiency Virus Type 1 Lipopeptide Vaccine: Characterization of CD8+-T-Cell Epitopes Recognized," Journal of Virology 77(20):11220-11231.
Genbank accession No. AAB62620, Oct. 2005.
Genbank accession No. AAL32169, Nov. 2001.
Genbank accession No. NP_626519, Apr. 2006.
Gianfrani et al. (2000) "Human Memory CTL Response Specific for Influenza A Virus is Broad and Multispecific," Hum. Immunol. 61:438-452.
Gileadi et al. (1999) "Effect of epitope flanking residues on the presentation of N-terminal cytotoxic T lymphocyte epitopes," Eur J Immunol. 29(7):2213-22.
Gileadi et al. (1999) "Generation of an Immunodominant CTL Epitope Is Affected by Proteasome Subunit Composition and Stability of the Antigenic Protein," J. Immunol. 163:6045-6052.

Gotch et al. (1987) "Cytotoxic T lymphocytes recognize a fragment of influenza virus matrix protein in association with HLA-A2," Nature 326:881-882.
Hackett et al. (2005) "Vaccine Adjuvants," Chapter 10 pp. 193-219.
Hall et al. (1981) "Variation in Nucleotide Sequences Coding for the N-terminal Regions of the Matrix and Nonstructural Proteins of Influenza A Viruses," J. Viral. 38(1):1-7.
HIV Databases (http://www.hiv.lanl.gov/content index) printed Oct. 3, 2007.
HIV Immunology Database: Compendia(http://www.hiv.lanl.gov/content/immunology/compendium.html) printed Oct. 3, 2007.
HIV Molecular Immunology Database (http://www.hiv.lanl.gov/content/immunology/index.html) printed Oct. 3, 2007.
Idemyor (2003) "Human immunodeficiency virus: scientific challenges impeding candidate vaccines," HIV Clin Trial, 4, 421-4.
International Search Report for International Application No. PCT/GB2007/000383 (PepTcell Limited), dated Sep. 14, 2007 and Reference cited therein: Database Uniprot Nov. 1, 1996 ( Nov. 1, 1996 ), Castrucci et al. "Genetic reassortment between avian and human influenza A virus," XP002442455 accession No. 067194. (Reference document includes manuscript on which Database entry is based) (10 pages).
International Search Report for PCT/GB2005/001279, dated Dec. 12, 2005 (7 pages).
International Search Report for PCT/GB2008/002930 (Immune Targeting Systems), dated Jan. 12, 2009 (3 pages).
Jameson et al. (1998) "Human cytotoxic T-lymphocyte repertoire to influenza A viruses," Journal of Virology, 72(11):8682-8689.
Jin et al. (2005) "Two residues in the hemagglutinin of A/Fujian/411/02-like influenza viruses are responsible for antigenic drift from A/Panama/2007/99," Virology 336:113-119.
Koch et al. (2005) "The crystal structure of human CD1d with and without alpha-galactosylceramide" Nature Immunology 6(8):819-26.
Korber et al. (2003) "HIV Immunology and HIV/SIV Vaccine Databases" pp. 343, 508, 661, 1042-1044.
Lawson et al. (1992) "Nucleotide Sequence Changes in the Polymerase Basic Protein 2 Gene of Temperature-Sensitive Mutants of Influenza A Virus," Virology 191:506-510.
Linnemann et al. (2000) "Detection and Quantification of CD4+ T Cells with Specificity for a New Major Histocompatibility Complex Class II-Restricted Influenza A Virus Matrix Protein Epitope in Peripheral Blood of Influenza Patients," J. Virol. 74(18):8740-8743.
Los Alamos National Laboratory Database (http://www.google.com) printed Oct. 3, 2007.
Lu et al. (2004) "Therapeutic dendritic-cell vaccine for chronic HIV-1 infection," Nature Medicine 10(12):1359-65.
Macken et al. (2001) "The value of a database in surveillance and vaccine selection" International Congress Series 1219:103-106.
Maksyutov et al. (1993) "ADEPT: a computer program for prediction of protein antigenic determinants," Comput. Appl. Biosci. 9(3):291-7.
Marsh et al. (2000) "The HLA Facts Book," Chapter 11 pp. 61-72.
Mortara et al. (1999) "Type 1 CD4+ T-Cell Help is Required for Induction of Antipeptide Multispecific Cytotoxic T Lymphocytes by a Lipopeptidic Vaccine in Rhesus Macaques," Journal of Virology 73(5):4447-4451.

* cited by examiner

SEQUENCE LISTING

<160> NUMBER OF SEQ ID NOS: 65

<210> SEQ ID NO 1
<211> LENGTH: 35
<212> TYPE: PRT
<213> ORGANISM: Influenza A virus

<400> SEQUENCE: 1

His Met Ala Ile Ile Lys Lys Tyr Thr Ser Gly Arg Gln Glu Lys Asn
1               5                   10                  15

Pro Ser Leu Arg Met Lys Trp Met Met Ala Met Lys Tyr Pro Ile Thr
            20                  25                  30

Ala Asp Lys
        35

<210> SEQ ID NO 2
<211> LENGTH: 35
<212> TYPE: PRT
<213> ORGANISM: Influenza A virus

<400> SEQUENCE: 2

Glu Arg Leu Lys His Gly Thr Phe Gly Pro Val His Phe Arg Asn Gln
1               5                   10                  15

Val Lys Ile Arg Arg Arg Val Asp Ile Asn Pro Gly His Ala Asp Leu
            20                  25                  30

Ser Ala Lys
        35

<210> SEQ ID NO 3
<211> LENGTH: 35
<212> TYPE: PRT
<213> ORGANISM: Influenza A virus

<400> SEQUENCE: 3

Ser Ala Lys Glu Ala Gln Asp Val Ile Met Glu Val Val Phe Pro Asn
1               5                   10                  15

Glu Val Gly Ala Arg Ile Leu Thr Ser Glu Ser Gln Leu Thr Ile Thr
            20                  25                  30

Lys Glu Lys
        35

<210> SEQ ID NO 4
<211> LENGTH: 35
<212> TYPE: PRT
<213> ORGANISM: Influenza A virus

<400> SEQUENCE: 4

Val Ala Tyr Met Leu Glu Arg Glu Leu Val Arg Lys Thr Arg Phe Leu
1               5                   10                  15

Pro Val Ala Gly Gly Thr Ser Ser Val Tyr Ile Glu Val Leu His Leu
            20                  25                  30

Thr Gln Gly
        35

<210> SEQ ID NO 5
<211> LENGTH: 35
<212> TYPE: PRT
<213> ORGANISM: Influenza A virus

<400> SEQUENCE: 5

Glu Val Arg Asn Asp Asp Val Asp Gln Ser Leu Ile Ile Ala Ala Arg

-continued

```
                1               5                  10                 15
Asn Ile Val Arg Arg Ala Ala Val Ser Ala Asp Pro Leu Ala Ser Leu
                20                 25                 30
Leu Glu Met
        35

<210> SEQ ID NO 6
<211> LENGTH: 35
<212> TYPE: PRT
<213> ORGANISM: Influenza A virus

<400> SEQUENCE: 6

Glu Gly Tyr Glu Glu Phe Thr Met Val Gly Arg Arg Ala Thr Ala Ile
1               5                  10                 15
Leu Arg Lys Ala Thr Arg Arg Leu Ile Gln Leu Ile Val Ser Gly Arg
                20                 25                 30
Asp Glu Gln
        35

<210> SEQ ID NO 7
<211> LENGTH: 35
<212> TYPE: PRT
<213> ORGANISM: Influenza A virus

<400> SEQUENCE: 7

Ala Thr Ala Ile Leu Arg Lys Ala Thr Arg Arg Leu Ile Gln Leu Ile
1               5                  10                 15
Val Ser Gly Arg Asp Glu Gln Ser Ile Ala Glu Ala Ile Ile Val Ala
                20                 25                 30
Met Val Phe
        35

<210> SEQ ID NO 8
<211> LENGTH: 35
<212> TYPE: PRT
<213> ORGANISM: Influenza A virus

<400> SEQUENCE: 8

Arg Gly Asp Leu Asn Phe Val Asn Arg Ala Asn Gln Arg Leu Asn Pro
1               5                  10                 15
Met His Gln Leu Leu Arg His Phe Gln Lys Asp Ala Lys Val Leu Phe
                20                 25                 30
Gln Asn Trp
        35

<210> SEQ ID NO 9
<211> LENGTH: 35
<212> TYPE: PRT
<213> ORGANISM: Influenza A virus

<400> SEQUENCE: 9

Ser Ser Ser Met Met Trp Glu Ile Asn Gly Pro Glu Ser Val Leu Val
1               5                  10                 15
Asn Thr Tyr Gln Trp Ile Ile Arg Asn Trp Glu Thr Val Lys Ile Gln
                20                 25                 30
Trp Ser Gln
        35

<210> SEQ ID NO 10
<211> LENGTH: 35
```

```
<212> TYPE: PRT
<213> ORGANISM: Influenza A virus

<400> SEQUENCE: 10

Tyr Ser Gly Phe Val Arg Thr Leu Phe Gln Gln Met Arg Asp Val Leu
1               5                   10                  15

Gly Thr Phe Asp Thr Val Gln Ile Ile Lys Leu Leu Pro Phe Ala Ala
                20                  25                  30

Ala Pro Pro
        35

<210> SEQ ID NO 11
<211> LENGTH: 35
<212> TYPE: PRT
<213> ORGANISM: Influenza A virus

<400> SEQUENCE: 11

Leu Gly Thr Phe Asp Thr Val Gln Ile Ile Lys Leu Leu Pro Phe Ala
1               5                   10                  15

Ala Ala Pro Pro Glu Gln Ser Arg Met Gln Phe Ser Ser Leu Thr Val
                20                  25                  30

Asn Val Arg
        35

<210> SEQ ID NO 12
<211> LENGTH: 33
<212> TYPE: PRT
<213> ORGANISM: Influenza A virus

<400> SEQUENCE: 12

Gln Ser Arg Met Gln Phe Ser Ser Leu Thr Val Asn Val Arg Gly Ser
1               5                   10                  15

Gly Met Arg Ile Leu Val Arg Gly Asn Ser Pro Val Phe Asn Tyr Asn
                20                  25                  30

Lys

<210> SEQ ID NO 13
<211> LENGTH: 35
<212> TYPE: PRT
<213> ORGANISM: Influenza A virus

<400> SEQUENCE: 13

Val Pro Ala Gln Asn Ala Ile Ser Thr Thr Phe Pro Tyr Thr Gly Asp
1               5                   10                  15

Pro Pro Tyr Ser His Gly Thr Gly Thr Gly Tyr Thr Met Asp Thr Val
                20                  25                  30

Asn Arg Thr
        35

<210> SEQ ID NO 14
<211> LENGTH: 35
<212> TYPE: PRT
<213> ORGANISM: Influenza A virus

<400> SEQUENCE: 14

Val Gln Gln Thr Arg Val Asp Lys Leu Thr Gly Gly Arg Gln Thr Tyr
1               5                   10                  15

Asp Trp Thr Leu Asn Arg Asn Gln Pro Ala Ala Thr Ala Leu Ala Asn
                20                  25                  30

Thr Ile Glu
```

<210> SEQ ID NO 15
<211> LENGTH: 35
<212> TYPE: PRT
<213> ORGANISM: Influenza A virus

<400> SEQUENCE: 15

Ser Tyr Leu Ile Arg Ala Leu Thr Leu Asn Thr Met Thr Lys Asp Ala
1               5                   10                  15

Glu Arg Gly Lys Leu Lys Arg Arg Ala Ile Ala Thr Pro Gly Met Gln
            20                  25                  30

Ile Arg Gly
        35

<210> SEQ ID NO 16
<211> LENGTH: 35
<212> TYPE: PRT
<213> ORGANISM: Influenza A virus

<400> SEQUENCE: 16

Glu Gln Ser Gly Leu Pro Val Gly Gly Asn Glu Lys Lys Ala Lys Leu
1               5                   10                  15

Ala Asn Val Val Arg Lys Met Met Thr Asn Ser Gln Asp Thr Glu Leu
            20                  25                  30

Ser Phe Thr
        35

<210> SEQ ID NO 17
<211> LENGTH: 35
<212> TYPE: PRT
<213> ORGANISM: Influenza A virus

<400> SEQUENCE: 17

Tyr Ile Thr Arg Asn Gln Pro Glu Trp Phe Arg Asn Val Leu Ser Ile
1               5                   10                  15

Ala Pro Ile Met Phe Ser Asn Lys Met Ala Arg Leu Gly Lys Gly Tyr
            20                  25                  30

Met Phe Glu
        35

<210> SEQ ID NO 18
<211> LENGTH: 35
<212> TYPE: PRT
<213> ORGANISM: Influenza A virus
<220> FEATURE:
<221> NAME/KEY: misc_feature
<222> LOCATION: (22)..(22)
<223> OTHER INFORMATION: Xaa can be any naturally occurring amino acid

<400> SEQUENCE: 18

Ala Pro Ile Met Phe Ser Asn Lys Met Ala Arg Leu Gly Lys Gly Tyr
1               5                   10                  15

Met Phe Glu Ser Lys Xaa Met Lys Leu Arg Thr Gln Ile Pro Ala Glu
            20                  25                  30

Met Leu Ala
        35

<210> SEQ ID NO 19
<211> LENGTH: 33
<212> TYPE: PRT
<213> ORGANISM: Influenza A virus

<400> SEQUENCE: 19

Ser Pro Gly Met Met Gly Met Phe Asn Met Leu Ser Thr Val Leu
1               5                   10                  15

Gly Val Ser Ile Leu Asn Leu Gly Gln Lys Lys Tyr Thr Lys Thr
            20                  25                  30

Tyr

<210> SEQ ID NO 20
<211> LENGTH: 35
<212> TYPE: PRT
<213> ORGANISM: Influenza A virus

<400> SEQUENCE: 20

Lys Lys Lys Ser Tyr Ile Asn Lys Thr Gly Thr Phe Glu Phe Thr Ser
1               5                   10                  15

Phe Phe Tyr Arg Tyr Gly Phe Val Ala Asn Phe Ser Met Glu Leu Pro
            20                  25                  30

Ser Phe Gly
        35

<210> SEQ ID NO 21
<211> LENGTH: 35
<212> TYPE: PRT
<213> ORGANISM: Influenza A virus

<400> SEQUENCE: 21

Lys Thr Gly Thr Phe Glu Phe Thr Ser Phe Phe Tyr Arg Tyr Gly Phe
1               5                   10                  15

Val Ala Asn Phe Ser Met Glu Leu Pro Ser Phe Gly Val Ser Gly Ile
            20                  25                  30

Asn Glu Ser
        35

<210> SEQ ID NO 22
<211> LENGTH: 35
<212> TYPE: PRT
<213> ORGANISM: Influenza A virus

<400> SEQUENCE: 22

Gly Val Thr Val Ile Lys Asn Asn Met Ile Asn Asn Asp Leu Gly Pro
1               5                   10                  15

Ala Thr Ala Gln Met Ala Leu Gln Leu Phe Ile Lys Asp Tyr Arg Tyr
            20                  25                  30

Thr Tyr Arg
        35

<210> SEQ ID NO 23
<211> LENGTH: 35
<212> TYPE: PRT
<213> ORGANISM: Influenza A virus

<400> SEQUENCE: 23

Glu Tyr Asp Ala Val Ala Thr Thr His Ser Trp Ile Pro Lys Arg Asn
1               5                   10                  15

Arg Ser Ile Leu Asn Thr Ser Gln Arg Gly Ile Leu Glu Asp Glu Gln
            20                  25                  30

Met Tyr Gln
        35

<210> SEQ ID NO 24
<211> LENGTH: 35
<212> TYPE: PRT
<213> ORGANISM: Influenza A virus

<400> SEQUENCE: 24

Phe Pro Ser Ser Ser Tyr Arg Arg Pro Val Gly Ile Ser Ser Met Val
1               5                   10                  15

Glu Ala Met Val Ser Arg Ala Arg Ile Asp Ala Arg Ile Asp Phe Glu
            20                  25                  30

Ser Gly Arg
        35

<210> SEQ ID NO 25
<211> LENGTH: 35
<212> TYPE: PRT
<213> ORGANISM: Influenza A virus

<400> SEQUENCE: 25

Pro Asp Leu Tyr Asp Tyr Lys Glu Asn Arg Phe Ile Glu Ile Gly Val
1               5                   10                  15

Thr Arg Arg Glu Val His Ile Tyr Tyr Leu Glu Lys Ala Asn Lys Ile
            20                  25                  30

Lys Ser Glu
        35

<210> SEQ ID NO 26
<211> LENGTH: 35
<212> TYPE: PRT
<213> ORGANISM: Influenza A virus

<400> SEQUENCE: 26

Val Thr Arg Arg Glu Val His Ile Tyr Tyr Leu Glu Lys Ala Asn Lys
1               5                   10                  15

Ile Lys Ser Glu Lys Thr His Ile His Ile Phe Ser Phe Thr Gly Glu
            20                  25                  30

Glu Met Ala
        35

<210> SEQ ID NO 27
<211> LENGTH: 35
<212> TYPE: PRT
<213> ORGANISM: Influenza A virus

<400> SEQUENCE: 27

Ile His Ile Phe Ser Phe Thr Gly Glu Glu Met Ala Thr Lys Ala Asp
1               5                   10                  15

Tyr Thr Leu Asp Glu Glu Ser Arg Ala Arg Ile Lys Thr Arg Leu Phe
            20                  25                  30

Thr Ile Arg
        35

<210> SEQ ID NO 28
<211> LENGTH: 35
<212> TYPE: PRT
<213> ORGANISM: Influenza A virus

<400> SEQUENCE: 28

Glu Ser Arg Ala Arg Ile Lys Thr Arg Leu Phe Thr Ile Arg Gln Glu
1               5                   10                  15

-continued

```
Met Ala Ser Arg Gly Leu Trp Asp Ser Phe Arg Gln Ser Glu Arg Gly
            20                  25                  30

Glu Glu Thr
        35

<210> SEQ ID NO 29
<211> LENGTH: 35
<212> TYPE: PRT
<213> ORGANISM: Influenza A virus

<400> SEQUENCE: 29

Arg Arg Lys Thr Asn Leu Tyr Gly Phe Ile Ile Lys Gly Arg Ser His
1               5                   10                  15

Leu Arg Asn Asp Thr Asp Val Val Asn Phe Val Ser Met Glu Phe Ser
            20                  25                  30

Leu Thr Asp
        35

<210> SEQ ID NO 30
<211> LENGTH: 35
<212> TYPE: PRT
<213> ORGANISM: Influenza A virus

<400> SEQUENCE: 30

Ala Lys Ser Val Phe Asn Ser Leu Tyr Ala Ser Pro Gln Leu Glu Gly
1               5                   10                  15

Phe Ser Ala Glu Ser Arg Lys Leu Leu Leu Ile Val Gln Ala Leu Arg
            20                  25                  30

Asp Asn Leu
        35

<210> SEQ ID NO 31
<211> LENGTH: 35
<212> TYPE: PRT
<213> ORGANISM: Influenza A virus

<400> SEQUENCE: 31

Pro Arg Arg Ser Gly Ala Ala Gly Ala Ala Val Lys Gly Val Gly Thr
1               5                   10                  15

Met Val Met Glu Leu Ile Arg Met Ile Lys Arg Gly Ile Asn Asp Arg
            20                  25                  30

Asn Phe Trp
        35

<210> SEQ ID NO 32
<211> LENGTH: 35
<212> TYPE: PRT
<213> ORGANISM: Influenza A virus

<400> SEQUENCE: 32

Asp Gln Val Arg Glu Ser Arg Asn Pro Gly Asn Ala Glu Ile Glu Asp
1               5                   10                  15

Leu Ile Phe Leu Ala Arg Ser Ala Leu Ile Leu Arg Gly Ser Val Ala
            20                  25                  30

His Lys Ser
        35

<210> SEQ ID NO 33
<211> LENGTH: 35
<212> TYPE: PRT
<213> ORGANISM: Influenza A virus
```

-continued

<400> SEQUENCE: 33

Ser Leu Leu Thr Glu Val Glu Thr Tyr Val Leu Ser Ile Ile Pro Ser
1               5                   10                  15

Gly Pro Leu Lys Ala Glu Ile Ala Gln Arg Leu Glu Asp Val Phe Ala
                20                  25                  30

Gly Lys Asn
        35

<210> SEQ ID NO 34
<211> LENGTH: 35
<212> TYPE: PRT
<213> ORGANISM: Influenza A virus

<400> SEQUENCE: 34

Glu Ile Ala Gln Arg Leu Glu Asp Val Phe Ala Gly Lys Asn Thr Asp
1               5                   10                  15

Leu Glu Ala Leu Met Glu Trp Leu Lys Thr Arg Pro Ile Leu Ser Pro
                20                  25                  30

Leu Thr Lys
        35

<210> SEQ ID NO 35
<211> LENGTH: 35
<212> TYPE: PRT
<213> ORGANISM: Influenza A virus

<400> SEQUENCE: 35

Asp Leu Glu Ala Leu Met Glu Trp Leu Lys Thr Arg Pro Ile Leu Ser
1               5                   10                  15

Pro Leu Thr Lys Gly Ile Leu Gly Phe Val Phe Thr Leu Thr Val Pro
                20                  25                  30

Ser Glu Arg
        35

<210> SEQ ID NO 36
<211> LENGTH: 35
<212> TYPE: PRT
<213> ORGANISM: Influenza A virus

<400> SEQUENCE: 36

Leu Thr Lys Gly Ile Leu Gly Phe Val Phe Thr Leu Thr Val Pro Ser
1               5                   10                  15

Glu Arg Gly Leu Gln Arg Arg Arg Phe Val Gln Asn Ala Leu Asn Gly
                20                  25                  30

Asn Gly Asp
        35

<210> SEQ ID NO 37
<211> LENGTH: 35
<212> TYPE: PRT
<213> ORGANISM: Influenza A virus

<400> SEQUENCE: 37

Ala Thr Thr Thr Asn Pro Leu Ile Arg His Glu Asn Arg Met Val Leu
1               5                   10                  15

Ala Ser Thr Thr Ala Lys Ala Met Glu Gln Met Ala Gly Ser Ser Glu
                20                  25                  30

Gln Ala Ala
        35

<210> SEQ ID NO 38
<211> LENGTH: 35
<212> TYPE: PRT
<213> ORGANISM: Influenza A virus

<400> SEQUENCE: 38

```
Ile Ile Leu Lys Ala Asn Phe Ser Val Ile Phe Asp Arg Leu Glu Thr
1               5                   10                  15

Leu Ile Leu Leu Arg Ala Phe Thr Glu Glu Gly Ala Ile Val Gly Glu
            20                  25                  30

Ile Ser Pro
        35
```

<210> SEQ ID NO 39
<211> LENGTH: 35
<212> TYPE: PRT
<213> ORGANISM: Influenza A virus

<400> SEQUENCE: 39

```
Glu Asp Leu Asn Gly Met Ile Thr Gln Phe Glu Ser Leu Lys Leu Tyr
1               5                   10                  15

Arg Asp Ser Leu Gly Glu Ala Val Met Arg Met Gly Asp Leu His Ser
            20                  25                  30

Leu Gln Asn
        35
```

<210> SEQ ID NO 40
<211> LENGTH: 35
<212> TYPE: PRT
<213> ORGANISM: Influenza B virus

<400> SEQUENCE: 40

```
Asn Glu Ala Lys Thr Val Leu Lys Gln Thr Thr Val Asp Gln Tyr Asn
1               5                   10                  15

Ile Ile Arg Lys Phe Asn Thr Ser Arg Ile Glu Lys Asn Pro Ser Leu
            20                  25                  30

Arg Met Lys
        35
```

<210> SEQ ID NO 41
<211> LENGTH: 35
<212> TYPE: PRT
<213> ORGANISM: Influenza B virus

<400> SEQUENCE: 41

```
Tyr Glu Ser Phe Phe Leu Arg Lys Met Arg Leu Asp Asn Ala Thr Trp
1               5                   10                  15

Gly Arg Ile Thr Phe Gly Pro Val Glu Arg Val Arg Lys Arg Val Leu
            20                  25                  30

Leu Asn Pro
        35
```

<210> SEQ ID NO 42
<211> LENGTH: 35
<212> TYPE: PRT
<213> ORGANISM: Influenza B virus

<400> SEQUENCE: 42

```
Glu Arg Val Arg Lys Arg Val Leu Leu Asn Pro Leu Thr Lys Glu Met
1               5                   10                  15
```

```
Pro Pro Asp Glu Ala Ser Asn Val Ile Met Glu Ile Leu Phe Pro Lys
            20                  25                  30

Glu Ala Gly
        35

<210> SEQ ID NO 43
<211> LENGTH: 35
<212> TYPE: PRT
<213> ORGANISM: Influenza B virus

<400> SEQUENCE: 43

Gly Thr Met Ile Thr Pro Ile Val Leu Ala Tyr Met Leu Glu Arg Glu
1               5                   10                  15

Leu Val Ala Arg Arg Arg Phe Leu Pro Val Ala Gly Ala Thr Ser Ala
            20                  25                  30

Glu Phe Ile
        35

<210> SEQ ID NO 44
<211> LENGTH: 35
<212> TYPE: PRT
<213> ORGANISM: Influenza B virus

<400> SEQUENCE: 44

Asp Ile Ile Arg Ala Ala Leu Gly Leu Lys Ile Arg Gln Arg Gln Arg
1               5                   10                  15

Phe Gly Arg Leu Glu Leu Lys Arg Ile Ser Gly Arg Gly Phe Lys Asn
            20                  25                  30

Asp Glu Glu
        35

<210> SEQ ID NO 45
<211> LENGTH: 35
<212> TYPE: PRT
<213> ORGANISM: Influenza B virus

<400> SEQUENCE: 45

Met Val Phe Ser Gln Asp Thr Arg Met Phe Gln Gly Val Arg Gly Glu
1               5                   10                  15

Ile Asn Phe Leu Asn Arg Ala Gly Gln Leu Leu Ser Pro Met Tyr Gln
            20                  25                  30

Leu Gln Arg
        35

<210> SEQ ID NO 46
<211> LENGTH: 35
<212> TYPE: PRT
<213> ORGANISM: Influenza B virus

<400> SEQUENCE: 46

Val Ser Glu Leu Glu Ser Gln Ala Gln Leu Met Ile Thr Tyr Asp Thr
1               5                   10                  15

Pro Lys Met Trp Glu Met Gly Thr Thr Lys Glu Leu Val Gln Asn Thr
            20                  25                  30

Tyr Gln Trp
        35

<210> SEQ ID NO 47
<211> LENGTH: 35
<212> TYPE: PRT
```

<213> ORGANISM: Influenza B virus

<400> SEQUENCE: 47

Met Trp Glu Met Gly Thr Thr Lys Glu Leu Val Gln Asn Thr Tyr Gln
1 5 10 15

Trp Val Leu Lys Asn Leu Val Thr Leu Lys Ala Gln Phe Leu Leu Gly
20 25 30

Lys Glu Asp
35

<210> SEQ ID NO 48
<211> LENGTH: 35
<212> TYPE: PRT
<213> ORGANISM: Influenza B virus

<400> SEQUENCE: 48

Met Phe Gln Trp Asp Ala Phe Glu Ala Phe Glu Ser Ile Ile Pro Gln
1 5 10 15

Lys Met Ala Gly Gln Tyr Ser Gly Phe Ala Arg Ala Val Leu Lys Gln
20 25 30

Met Arg Asp
35

<210> SEQ ID NO 49
<211> LENGTH: 35
<212> TYPE: PRT
<213> ORGANISM: Influenza B virus

<400> SEQUENCE: 49

Leu Glu Lys Leu Lys Pro Gly Glu Lys Ala Asn Ile Leu Leu Tyr Gln
1 5 10 15

Gly Lys Pro Val Lys Val Val Lys Arg Lys Arg Tyr Ser Ala Leu Ser
20 25 30

Asn Asp Ile
35

<210> SEQ ID NO 50
<211> LENGTH: 35
<212> TYPE: PRT
<213> ORGANISM: Influenza B virus

<400> SEQUENCE: 50

Met Asn Ile Asn Pro Tyr Phe Leu Phe Ile Asp Val Pro Ile Gln Ala
1 5 10 15

Ala Ile Ser Thr Thr Phe Pro Tyr Thr Gly Val Pro Pro Tyr Ser His
20 25 30

Gly Thr Gly
35

<210> SEQ ID NO 51
<211> LENGTH: 35
<212> TYPE: PRT
<213> ORGANISM: Influenza B virus

<400> SEQUENCE: 51

Glu Glu His Pro Gly Leu Phe Gln Ala Ala Ser Gln Asn Ala Met Glu
1 5 10 15

Ala Leu Met Val Thr Thr Val Asp Lys Leu Thr Gln Gly Arg Gln Thr
20 25 30

Phe Asp Trp

<210> SEQ ID NO 52
<211> LENGTH: 35
<212> TYPE: PRT
<213> ORGANISM: Influenza B virus

<400> SEQUENCE: 52

Met Thr Lys Asp Ala Glu Arg Gly Lys Leu Lys Arg Arg Ala Ile Ala
1               5                   10                  15

Thr Ala Gly Ile Gln Ile Arg Gly Phe Val Leu Val Val Glu Asn Leu
            20                  25                  30

Ala Lys Asn
        35

<210> SEQ ID NO 53
<211> LENGTH: 35
<212> TYPE: PRT
<213> ORGANISM: Influenza B virus

<400> SEQUENCE: 53

Lys Pro Phe Phe Asn Glu Glu Gly Thr Ala Ser Leu Ser Pro Gly Met
1               5                   10                  15

Met Met Gly Met Phe Asn Met Leu Ser Thr Val Leu Gly Val Ala Ala
            20                  25                  30

Leu Gly Ile
        35

<210> SEQ ID NO 54
<211> LENGTH: 35
<212> TYPE: PRT
<213> ORGANISM: Influenza B virus

<400> SEQUENCE: 54

Asp Pro Glu Tyr Lys Gly Arg Leu Leu His Pro Gln Asn Pro Phe Val
1               5                   10                  15

Gly His Leu Ser Ile Glu Gly Ile Lys Glu Ala Asp Ile Thr Pro Ala
            20                  25                  30

His Gly Pro
        35

<210> SEQ ID NO 55
<211> LENGTH: 35
<212> TYPE: PRT
<213> ORGANISM: Influenza B virus

<400> SEQUENCE: 55

Ser Ala Ser Tyr Arg Lys Pro Val Gly Gln His Ser Met Leu Glu Ala
1               5                   10                  15

Met Ala His Arg Leu Arg Met Asp Ala Arg Leu Asp Tyr Glu Ser Gly
            20                  25                  30

Arg Met Ser
        35

<210> SEQ ID NO 56
<211> LENGTH: 35
<212> TYPE: PRT
<213> ORGANISM: Influenza B virus

<400> SEQUENCE: 56

Ser Ser Leu Asp Glu Glu Gly Lys Gly Arg Val Leu Ser Arg Leu Thr

```
1               5                   10                  15
Glu Leu Gln Ala Glu Leu Ser Leu Lys Asn Leu Trp Gln Val Leu Ile
                20                  25                  30

Gly Glu Glu
        35

<210> SEQ ID NO 57
<211> LENGTH: 35
<212> TYPE: PRT
<213> ORGANISM: Influenza B virus

<400> SEQUENCE: 57

Glu Ser Phe Asp Met Leu Tyr Gly Leu Ala Val Lys Gly Gln Ser His
1               5                   10                  15

Leu Arg Gly Asp Thr Asp Val Val Thr Val Val Thr Phe Glu Phe Ser
                20                  25                  30

Ser Thr Asp
        35

<210> SEQ ID NO 58
<211> LENGTH: 31
<212> TYPE: PRT
<213> ORGANISM: Influenza B virus

<400> SEQUENCE: 58

Val Ile Gln Ser Ala Tyr Trp Phe Asn Glu Trp Leu Gly Phe Glu Lys
1               5                   10                  15

Glu Gly Ser Lys Val Leu Glu Ser Val Asp Glu Ile Met Asp Glu
                20                  25                  30

<210> SEQ ID NO 59
<211> LENGTH: 35
<212> TYPE: PRT
<213> ORGANISM: Influenza B virus

<400> SEQUENCE: 59

Phe Leu Lys Glu Glu Val Lys Thr Met Tyr Lys Thr Thr Met Gly Ser
1               5                   10                  15

Asp Gly Phe Ser Gly Leu Asn His Ile Met Ile Gly His Ser Gln Met
                20                  25                  30

Asn Asp Val
        35

<210> SEQ ID NO 60
<211> LENGTH: 35
<212> TYPE: PRT
<213> ORGANISM: Influenza B virus

<400> SEQUENCE: 60

Glu Ala Ile Arg Phe Ile Gly Arg Ala Met Ala Asp Arg Gly Leu Leu
1               5                   10                  15

Arg Asp Ile Lys Ala Lys Thr Ala Tyr Glu Lys Ile Leu Leu Asn Leu
                20                  25                  30

Lys Asn Lys
        35

<210> SEQ ID NO 61
<211> LENGTH: 35
<212> TYPE: PRT
<213> ORGANISM: Influenza B virus
```

-continued

<400> SEQUENCE: 61

Ile Ala Asp Ile Glu Asp Leu Thr Leu Leu Ala Arg Ser Met Val Val
1               5                   10                  15

Val Arg Pro Ser Val Ala Ser Lys Val Val Leu Pro Ile Ser Ile Tyr
            20                  25                  30

Ala Lys Ile
        35

<210> SEQ ID NO 62
<211> LENGTH: 35
<212> TYPE: PRT
<213> ORGANISM: Influenza B virus

<400> SEQUENCE: 62

Ile Tyr Ala Lys Ile Pro Gln Leu Gly Phe Asn Val Glu Glu Tyr Ser
1               5                   10                  15

Met Val Gly Tyr Glu Ala Met Ala Leu Tyr Asn Met Ala Thr Pro Val
            20                  25                  30

Ser Ile Leu
        35

<210> SEQ ID NO 63
<211> LENGTH: 35
<212> TYPE: PRT
<213> ORGANISM: Influenza B virus

<400> SEQUENCE: 63

Gly Phe His Val Pro Ala Lys Glu Gln Val Glu Gly Met Gly Ala Ala
1               5                   10                  15

Leu Met Ser Ile Lys Leu Gln Phe Trp Ala Pro Met Thr Arg Ser Gly
            20                  25                  30

Gly Asn Glu
        35

<210> SEQ ID NO 64
<211> LENGTH: 35
<212> TYPE: PRT
<213> ORGANISM: Influenza B virus

<400> SEQUENCE: 64

Ala Arg Ser Ser Val Pro Gly Val Arg Arg Glu Met Gln Met Val Ser
1               5                   10                  15

Ala Met Asn Thr Ala Lys Thr Met Asn Gly Met Gly Lys Gly Glu Asp
            20                  25                  30

Val Gln Lys
        35

<210> SEQ ID NO 65
<211> LENGTH: 29
<212> TYPE: PRT
<213> ORGANISM: Influenza B virus

<400> SEQUENCE: 65

Ile Gly Val Leu Arg Ser Leu Gly Ala Ser Gln Lys Asn Gly Glu Gly
1               5                   10                  15

Ile Ala Lys Asp Val Met Glu Val Leu Lys Gln Ser Ser
            20                  25

INFLUENZA ANTIGEN DELIVERY VECTORS AND CONSTRUCTS

RELATED APPLICATIONS

This application is a continuation application of U.S. application Ser. No. 14/139,293 filed Dec. 23, 2013, which is a continuation application of U.S. application Ser. No. 12/201,894, filed Aug. 29, 2008, now U.S. Pat. No. 8,642,531, which claims the benefit of and priority to U.S. Provisional Patent Application Ser. No. 60/969,481 filed Aug. 31, 2007. This application also claims the benefit of and priority to Great Britain Patent Application Serial No. GB0716992.3 filed Aug. 31, 2007. The entire disclosure of each application is incorporated herein by reference.

FIELD OF THE INVENTION

The present invention relates to fluorocarbon vectors for the delivery of influenza antigens to immunoresponsive target cells. It further relates to fluorocarbon vector-influenza antigen constructs and the use of such vectors associated with antigens as vaccines and immunotherapeutics in animals, including humans.

BACKGROUND

Influenza is the generic term for diseases or infections caused by the influenza virus. Influenza viruses are members of the Orthomyxoviridae family of viruses and comprise two genera: influenza A and B viruses, and influenza C virus. Influenza A, B and C viruses are distinguished on the basis of their internal nucleoprotein and matrix proteins which are specific for each viral type. Influenza A viruses are naturally able to infect a range of animal species, including humans, swine, birds, seals and horses. Influenza B viruses, however, infect only humans, whilst influenza C virus infects humans and swine. Influenza A viruses are further categorised into subtypes that are determined by the antigenicity of the surface glycoproteins, the haemagglutinin (H) and neuraminidase (N).

Historically, influenza A human infections have been caused by three subtypes of haemagglutinin (H1, H2 and H3) and two neuraminidase subtypes (N1 and N2); more recently human infections by the previously avian-restricted subtypes H5, H7 and H9 have also been reported. A total of 16 distinct haemagglutinin and 9 neuraminidase influenza A subtypes have been identified to date; these are all prevalent in birds. Swine and horses, like humans, are limited to a much narrower range of subtypes.

Influenza A and B virions are pleiomorphic in structure, spherical examples being 80-120 nm in diameter, whilst filamentous forms may be up to 300 nm in length. There are approximately 500 surface spike glycoproteins per particle (usually in the ratio of four to five haemagglutinin proteins to one neuraminidase) that are embedded in a host-derived lipid bilayer membrane. Within the membrane is the transmembrane ion channel protein M2, whilst the structural protein M1 underlies the bilayer. Within the core of the virus, the single stranded negative sense RNA is associated with the six other viral proteins expressed from its genome: the nucleoprotein (NP), three transcriptases (PB2, PB1, and PA) and two nonstructural proteins (NS1 and NS2). The influenza virus genome comprises eight segments; a feature that enables "gene swapping" reassortment. The haemagglutinin enables the virus to bind to host cell receptors and facilitates the entry of the virus into the cell where it will replicate. The neuraminidase protein enzymatically cleaves terminal sialic acid residues, and is believed to assist in the transport of the virus through the mucin layer of the respiratory tract as well as facilitating the budding of the progeny virus away from the host cell. Influenza C viruses, which present much less of a health-risk to humans possess a single surface protein which combines the haemagglutinin, fusion activity and receptor destroying activity.

As a result of the error prone RNA polymerase enzyme, both the haemagglutinin and neuraminidase proteins of the influenza virus are liable to point mutations which need not necessarily affect the ability of the virus to replicate. Such a mutation (or coincident mutations) at one of the sites recognised by the host antibody response may result in the host antibody, induced by vaccination or a previous infection, being unable to bind effectively to the "new" virus strain thereby allowing an infection to persist. As the human influenza strains are continually evolving via these point mutations, the virus is able to escape from the limited antibody repertoire of the human immune response and cause epidemics. The regular "seasonal" bouts of influenza infections are therefore caused by the circulating strains in the population undergoing antigenic drift.

During seasonal epidemics influenza can spread around the world quickly and inflicts a significant economic burden in terms of hospital and other healthcare costs and lost productivity. The virus is transmitted in droplets in the air from human-to-human and targets epithelial cells in the trachea and bronchi of the upper respiratory tract. Influenza virus may also be picked up from contaminated surfaces and passed to the mouth. Disease spreads very quickly especially in crowded circumstances through coughing and sneezing. The stability of the virus is favored by low relative humidity and low temperatures and, as a consequence, seasonal epidemics in temperate areas tend to appear in winter. Greater morbidity and mortality is observed with influenza A strains, with influenza B usually associated with lower attack rates and a milder disease. Occasionally, however, influenza B can cause epidemics of the same severity as type A viruses. Influenza B is primarily a childhood pathogen and does not usually exhibit the same degree of antigenic variation as type A.

The typical uncomplicated influenza infection is characterised by a rapid onset of illness (headache, cough, chills) followed by fever, sore throat, significant myalgias, malaise and loss of appetite. Further symptoms may include rhinorrhoea, substernal tightness and ocular symptoms. The most prominent sign of infection is the fever that is usually in the 38-40° C. temperature range. Whilst the majority of people will recover from influenza infection within one to two weeks without requiring any medical treatment, for certain members of the population the disease may present a serious risk. Such individuals include the very young, the elderly and people suffering from medical conditions such as lung diseases, diabetes, cancer, kidney or heart problems. In this "at risk" population, the infection may lead to severe complications of underlying diseases, bacterial pneumonia, (caused by respiratory pathogens such as *Streptococcus pneumoniae*, *Haemophilus influenzae* and *Staphylococcus aureus*) and death. The clinical features of influenza infection are similar in children, although their fever may be higher and febrile convulsions can occur. In addition, children have a higher incidence of vomiting and abdominal pain as well as otitis media complications, croup and myositis.

The World Health Organization estimates that in annual influenza epidemics 5-15% of the population is affected with upper respiratory tract infections. Hospitalization and deaths mainly occur in high-risk groups (elderly and the chronically ill). Although difficult to assess, these annual epidemics are thought to result in between three and five million cases of severe illness and approximately 250 000 and 500 000 deaths every year around the world. Over 90% of the deaths currently associated with influenza in industrialized countries occur among the elderly over 65 years of age. In the U.S.A., the CDC estimate that more than 200,000 people are hospitalized every year on average following complications arising from seasonal influenza infection, with around 36,000 excess mortalities being recorded.

The host immune response that controls the recovery from influenza infection is conferred through a combination of serum antibodies directed to the surface proteins, mucosal secretory IgA antibodies and cell-mediated immune responses. About one to two weeks after a primary infection, neutralizing haemagglutination inhibiting (HAI) antibodies as well as antibodies to neuraminidase are detectable in the serum, peaking at approximately three to four weeks. After re-infection, the antibody response is more rapid. Influenza antibodies may persist for months or years, although in some high-risk groups antibody levels can begin to decline within a few months after vaccination. Secretory IgA antibodies peak approximately 14 days after infection and can be detected in saliva, nasal secretions, sputum and in tracheal washings. Preceding the occurrence of antibody-producing cells, cytotoxic T lymphocytes with specificity for influenza appear, and serve to limit the infection by reducing the maximal viral load whilst mediating more rapid viral clearance through the induction of antiviral cytokines and lysing infected cells. In addition, mononuclear cells infiltrate infected airways providing antibody dependent cell-mediated cytotoxicity against influenza-infected cells.

To date, vaccines approaches against respiratory virus infections such as influenza essentially rely upon the induction of antibodies that protect against viral infection by neutralizing virions or blocking the virus's entry into cells. These humoral immune responses target external viral surface proteins that are conserved for a given strain. Antibody-mediated protection is therefore effective against homologous viral strains but inadequate against heterologous strains with serologically distinct surface proteins. This distinction is of consequence since the surface proteins of many viruses are capable of rapid mutation; for example an effective humoral response-based vaccine against a form of the influenza virus may be ineffective against next season's variant.

There are currently two main types of licensed influenza vaccines. One group of vaccines contains the haemagglutinin and neuraminidase surface proteins of the virus as the active immunogens. These include whole inactivated virus vaccines, split virus vaccines consisting of inactivated virus particles disrupted by detergent treatment, subunit vaccines consisting essentially purified surface proteins from which other virus components have been removed and virosomes where the surface proteins are presented on a liposomal surface. The second group comprises the live attenuated, cold-adapted, strains of virus. For all these vaccines a blend of surface antigens from usually three or four virus strains are required; current commercial influenza vaccines contain antigens from two A subtypes, H3N2 and H1N1, and one type B virus. Each year in September and February respectively, the WHO Global Influenza Program recommends the composition of the influenza vaccine for the next season that normally begins in May-June in the southern hemisphere and in November-December in the northern hemisphere. The composition is based on surveillance data from the worldwide network of national influenza centers and WHO collaborating centers and attempts to cover the likely strains to be circulating nine months later. For this reason, manufacturers are obliged to change the composition of the influenza vaccine on an annual basis in order to ensure an accurate match is achieved with the circulating viral strains.

Most inactivated influenza vaccines are given via the intramuscular route in the deltoid muscle, except in infants where the recommended site is the antero-lateral aspect of the thigh. A single dose of inactivated vaccine annually is appropriate, except for previously unvaccinated preschool children with pre-existing medical conditions who should receive two doses at least one month apart. The live attenuated influenza vaccine (LAIV) is delivered intra-nasally. These have been available in Russia for a number of years and recently licensed for use in the USA in pediatric populations. Such vaccines are able to elicit local antibody and cell-mediated immune responses at the nasal epithelial surface. The live attenuated influenza vaccine is not, however, licensed for use in the USA in elderly populations (over 50 years old).

To enhance the breadth and intensity of the immune response mounted to the influenza virus surface proteins, various adjuvants and alternative immuno-potentiating agents have been evaluated for inclusion in the vaccine formulation. An adjuvant in this context is an agent that is able to modulate the immune response directed to a co-administered antigen while having few if any direct effects when given on its own. Recent licensed developments in the influenza vaccine field include MF-59, a submicron oil-in water emulsion. Aluminium-containing adjuvants are also used by some manufacturers. The intention of these adjuvants is to amplify the resulting serum antibody response to the administered antigens.

Provided there is a good antigenic match between the vaccine strains and those circulating in the general population, inactivated influenza vaccines prevent laboratory-confirmed illness in approximately 70%-90% of healthy adults. However, the CDC highlights that vaccine efficacy in the elderly (over 65 years old) can be as low as 30-40%. Of relevance in this regard is the observation that ageing in humans creates defects in memory T-cell responses that reduce vaccine efficacy and increases the risk to natural infection. Furthermore, a clinical study in a community based setting demonstrated that cell mediated immunity, and not humoral immunity, was correlated with influenza disease protection in a group of over 60 year olds.

In addition, efficacy rates decline significantly if the vaccine strain is antigenically different to the circulating strains. Antigenic variation studies have indicated that four or more amino acid substitutions over at least two antigenic sites of the influenza A haemagglutinin results in a drift variant sufficiently discrete to undermine a vaccine's efficacy (Jin et al. "Two residues in the hemagglutinin of A/Fujian/411/02-like influenza viruses are responsible for antigenic drift from A/Panama/2007/99." Virology. 2005; 336:113-9). In a case controlled study of adults aged 50-64 years with laboratory confirmed influenza during the 2003-04 season when the vaccine and circulating A/H3N2 strains were not well matched, vaccine effectiveness was estimated to be 52% among healthy individuals and 38% among those with one or more high-risk conditions, according to the CDC. The likelihood of mismatching is raised by the limited manufacturing window of opportunity; the time from strain confirmation, through seed production, antigen manufacture and purification, and the trivalent blending and product filling must all occur in typically less than six months.

Occasionally, a new influenza strain emerges in the population with high pathogenicity and antigenic novelty which results in a worldwide pandemic. Pandemic influenza is the result of an antigenic shift in the surface proteins and represents a serious threat to global health as no pre-existing immunity has been developed by individuals. Pandemic strains are characterised by their sudden emergence in the population and their antigenic novelty. During the twentieth century, four pandemics occurred; in 1918 the causative strain was H1N1, in 1957 H2N2, in 1968 H3N2 and in 1977 H1N1.

There are three alternative explanations for the occurrence of antigenic shift. Firstly, as the influenza virus genome is segmented, it is possible for two influenza strains to exchange their genes upon co-infection of a single host, for example swine, leading to the construction of a replication-competent progeny carrying genetic information of different parental viruses. This process, known as genetic reassortment, is believed to have been the cause of the 1957 and 1968 pandemics. The 1968 pandemic arose when the H3 haemagglutinin gene and one other internal gene from an avian donor reassorted with the N2 neuraminidase and five other genes from the H2N2 human strain that had been in circulation. Secondly, a non-human influenza strain acquires the ability to infect humans. The 1918 pandemic arose when an avian H1N1 strain mutated to enable its rapid and efficient transfer from human-to-human. Thirdly, a strain that had previously caused an epidemic may remain sequestered and unaltered within the human population. The 1977 H1N1 pandemic strain, for example, was essentially identical to a strain that had caused an epidemic 27 years previously and was undetected in the human and animal reservoir over the intervening years.

An influenza pandemic is threatened once three principal criteria have been met:
1. An influenza virus HA subtype, unseen in the human population for at least one generation, emerges (or re-emerges).
2. The virus infects and replicates efficiently in humans, causing significant illness.
3. The virus is transmitted readily and sustainably between humans.

Global pandemics can afflict between 20% and 40% of the world's population in a single year. The pandemic of 1918-19, for example, affected 200 million people, killing over 30 million worldwide. In the United States, more than half a million individuals died, which represented 0.5% of the population. Although healthcare has dramatically improved since that time, with vaccines and antiviral therapies being developed, the CDC estimate that a pandemic today would result in two to seven million deaths globally.

Since 1999, three different influenza subtype strains (H5N1, H7N7 and H9N2) have crossed from avian species to humans, all causing human mortality. As of Aug. 14, 2007 a total of 320 human cases of H5N1 Highly Pathogenic Avian Influenza Virus (HPAIV) infection had been recorded worldwide, with 193 deaths.

Unlike normal seasonal influenza, where infection causes only mild respiratory symptoms in most healthy people, the disease caused by H5N1 follows an unusually aggressive clinical course, with rapid deterioration and high fatality. Primary viral pneumonia and multi-organ failure are common. It is significant that most cases have occurred in previously healthy children and young adults. H5N1 HPAIV incubates longer than other human influenza viruses before causing symptoms, up to eight days in some cases. In household clusters of cases, the time between cases has generally ranged from two to five days but has been reported to take as long as 17 days.

Initial symptoms of H5N1 HPAIV infection are more likely to include diarrhea and can appear up to a week before any respiratory symptoms. This feature, combined with the detection of viral RNA in stool samples, suggests that the virus can multiply in the gastrointestinal tract. Lower respiratory tract symptoms such as shortness of breath appear early in the course of the illness, whereas upper respiratory symptoms such as rhinorrheoa are less common.

H5N1 HPAIV presently meets two of the conditions required for a pandemic; the H5 haemagglutinin represents a new antigen for humans. No one will have immunity should an H5N1-like pandemic virus emerge. In addition, the virus has infected more than 300 humans, with an apparent mortality rate of over 60%.

All prerequisites for the start of a pandemic have therefore been met save one: the establishment of efficient and sustained human-to-human transmission of the virus. The risk that the H5N1 virus will acquire this ability will persist as long as opportunities for human infections occur. This is believed to be a realistic probability, either through step-wise mutation or through reassortment with a human-adapted strain.

At the scientific level, one or more changes to the virus phenotype are necessary before the virus strain could achieve ready human-to-human transmission and begin a pandemic. However, a number of recent observations including specific mutations detected in recent human isolates from Turkey, the increasing pathogenicity to mammals of the circulating virus, the expansion of the H5N1 HPAIV host range to include other mammals, such as tigers and cats that were previously considered to be resistant to infection with avian influenza viruses, all indicate that the H5N1 virus is continuing to evolve capabilities that may ultimately facilitate human-to-human transmission.

Other influenza viruses with possibly even greater pandemic potential may yet emerge. These include a number of H9 and H7 virus strains, which in recent years have also been transmitted to humans. H9 viruses are now endemic in poultry in Asia and also have crossed efficiently into pig populations in South Eastern and Eastern China. Of concern is the fact that the H9N2 strains possess typical human-like receptor specificity and have a broad host range.

In early 2003, an H7N7 HPAIV outbreak occurred in poultry in the Netherlands. Bird-to-human transmission of the H7N7 virus occurred in at least 82 cases. Conjunctivitis was the most common disease symptom in people infected with the H7 strain, with only seven cases displaying typical influenza-like illness. The virus did not prove highly pathogenic for humans and only one fatal case was observed. Other viruses with pandemic potential are those of the H2 subtype, because of its past history as a pandemic virus, and H6 because of its high incidence in poultry species in Asia and North America.

This indicates that a threat of a new human influenza pandemic is not uniquely linked to the emergence of HPAI H5N1.

In preparation for an influenza pandemic a number of clinical trials with candidate H5N1 influenza vaccines have been conducted. These have consistently shown that in order to generate a serum antibody response predicted to be protective, multiple doses of either a much higher amount of haemagglutinin antigen than is normally used in a seasonal vaccine or the inclusion of an adjuvant is required. This is a direct reflection of the immunological naivety of the population to the H5 haemagglutinin. At the present, the only options available for a pandemic influenza vaccine are therefore either one with a very high HA content, which would severely limit the number of doses that could be produced, or the use of an adjuvant that is not currently licensed in the majority of countries. It should also be appreciated that a vaccine that matches the pandemic strain will take many months to manufacture from the time that it is first isolated in humans; a stockpiled vaccine produced in advance of the emergence of a pandemic will most probably not be antigenically identical and therefore provide only limited protection, if any at all. Evidence of antigenic drift is already evident in the most recent outbreaks of H5N1.

In summary, there is a clear requirement for both seasonal and pandemic influenza vaccines to be improved:
1. There are obvious limitations in their efficacy, in particular in unprimed individuals. This is of specific concern with regard to the prospects of an influenza pandemic arising from antigenic shift.
2. The dependence on being able to predict accurately the influenza strains likely to be circulating in the following fall/winter seasons. A mismatch between the vaccine strains and those actually causing infections will render a significant proportion of the population vulnerable to influenza.
3. The need to re-vaccinate at risk groups on a yearly basis as the virus undergoes antigenic drift.
4. Capacity constraints, as there are only a limited number of potential biological manufacturing plants worldwide.
5. The protection afforded to the elderly age group is limited by conventional vaccines.

Improved classes of influenza vaccine therefore are needed, which are preferably synthetic, stable, and effective against all influenza A strains (including potential pandemic strains), with enhanced efficacy in the elderly (at risk) groups.

SUMMARY OF THE INVENTION

The present invention seeks to overcome the problem of delivering influenza antigens to immune responsive cells by using a fluorocarbon vector in order to enhance their immunogenicity. The fluorocarbon vector may comprise one or more chains derived from perfluorocarbon or mixed fluorocarbon/hydrocarbon radicals, and may be saturated or unsaturated, each chain having from 3 to 30 carbon atoms.

Accordingly, in one aspect, the invention provides a fluorocarbon vector-antigen construct of structure $C_mF_n$—$C_yH_x$-(Sp)-R or derivatives thereof, where m=3 to 30, n<=2m+1, y=0 to 15, x<=2y, (m+y)=3-30, Sp is an optional chemical spacer moiety and R is an antigen derived from the influenza virus. In another aspect, the invention provides a fluorocarbon vector-antigen construct of structure $$F_3C-CF_2-CF_2-CF_2-CF_2-CF_2-CF_2-CF_2-Sp-R$$

where Sp is an optional chemical spacer moiety and R is an antigen derived from the influenza virus. These aspects of the invention can have one or more of the following features. R can include one or more epitopes from an influenza virus protein. R can include one or more epitopes from an influenza virus type A protein or an influenza virus type B protein or an influenza virus type C protein. R can be a peptide, optionally an immunogenic peptide. R can be a peptide of between 7 to 100 amino acids. R can include at least one MHC class I or II binding epitope or B cell binding epitope, or combinations thereof. R can include two or more overlapping epitopes. R can be a peptide selected from the NCBI and Los Alamos National Laboratory influenza sequence databases or fragments, derivatives, homologues or combinations thereof. R can be a peptide selected from SEQ ID Nos 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, or 65 or fragments, derivatives, homologues or combinations thereof. The fluorocarbon vector can be non-covalently associated with an antigen. R can include multiple epitopes and/or fusion peptides.

Moreover, the present invention provides a pharmaceutical composition that includes one or more fluorocarbon vector-antigen constructs described above, optionally together with one or more pharmaceutically acceptable carriers, excipients, diluents or adjuvants. The pharmaceutical composition can be formulated for parenteral, oral, ocular, rectal, nasal, transdermal, topical, or vaginal administration. The pharmaceutical composition can take the form of a liquid, emulsion, solid, aerosol or gas. The pharmaceutical composition can be in combination with an adjuvant selected from: (1) natural or synthetically derived refinements of natural components of bacteria such as Freund's adjuvant and its derivatives, muramyldipeptide (MDP) derivatives, CpG, monophosphoryl lipid A; (2) adjuvants or potentiating agents such as saponins, aluminium salts and cytokines; (3) oil in water adjuvants, water-in-oil adjuvants, immunostimulating complex (ISCOMs), liposomes, formulated nano and micro-particles; and (4) bacterial toxins and toxoids. The pharmaceutical composition can include more than one (e.g. at least two) vector-antigen constructs, and the first construct can include the influenza peptide sequence:

```
                                          (SEQ ID NO: 1)
HMAIIKKYTSGRQEKNPSLRMKWMMAMKYPITADK
``` and the second construct comprising the influenza peptide sequence:

```
                                         (SEQ ID NO: 17)
YITRNQPEWFRNVLSIAPIMFSNKMARLGKGYMFE.
```

For example, the pharmaceutical composition can include 8 vector-antigen constructs that include the following influenza peptide sequences:

```
Construct 1 -
                                          (SEQ ID NO: 1)
HMAIIKKYTSGRQEKNPSLRMKWMMAMKYPITADK;

Construct 2 -
                                          (SEQ ID NO: 4)
VAYMLERELVRKTRFLPVAGGTSSVYIEVLHLTQG;

Construct 3 -
                                         (SEQ ID NO: 17)
YITRNQPEWFRNVLSIAPIMFSNKMARLGKGYMFE;

Construct 4 -
                                         (SEQ ID NO: 18)
APIMFSNKMARLGKGYMFESKXMKLRTQIPAEMLA, where X can be R or S;
```

```
Construct 5 -
                                            (SEQ ID NO: 19)
SPGMMMGMFNMLSTVLGVSILNLGQKKYTKTTY;

Construct 6 -
                                            (SEQ ID NO: 20)
KKKSYINKTGTFEFTSFFYRYGFVANFSMELPSFG;

Construct 7 -
                                            (SEQ ID NO: 32)
DQVRESRNPGNAEIEDLIFLARSALILRGSVAHKS;

Construct 8 -
                                            (SEQ ID NO: 35)
DLEALMEWLKTRPILSPLTKGILGFVFTLTVPSER.
```

The pharmaceutical composition can be administered in combination with a humoral response-based influenza vaccine, either contemporaneously or separately. For example, the pharmaceutical composition can be a haemagglutinin containing influenza vaccine.

In another aspect, the invention provides a use of one or more of the fluorocarbon vector-antigen constructs described above in the preparation of a prophylactic vaccine or immunotherapeutic pharmaceutical product. The prophylactic vaccine or immunotherapeutic pharmaceutical product can be for parenteral, mucosal, oral, nasal, topical, ocular, rectal, transdermal, or vaginal administration. The method of preparing a prophylactic or therapeutic pharmaceutical product can include combining one or more fluorocarbon constructs described above with one or more pharmaceutically acceptable carriers, excipients, diluents, or adjuvants, optionally for parenteral, mucosal, oral, nasal, topical, ocular, rectal, transdermal, or vaginal administration.

In other aspect, the invention provides a method of using one or more of the compositions described above. This aspect of the invention can have one or more of the following features. The method can include treatment or immunization using any of the compositions described above. The method can include stimulating an immune response, including administering the formulation of any of the compositions described above to an animal, such as a bird, a mammal, or a human. The method can include administering a pharmaceutical composition described above, in combination with anti-influenza therapy, such as administration of a neuraminidase inhibitor. The method can include stimulating an immune response by administering any of the preventative or therapeutic formulations described above, in combination with a haemagglutinin containing influenza vaccine, either contemporaneously or separately.

It should be understood that different features and embodiments of the invention, including those described under different aspects of the invention, are meant to be generally applicable to all aspects of the invention. Any embodiment may be combined with any other embodiment unless inappropriate. All examples are illustrative and non-limiting.

BRIEF DESCRIPTION OF THE DRAWINGS

The foregoing aspects and embodiments of the invention may be more fully understood by reference to the following detailed description and claims.

FIG. 1 shows a comparison of the immunogenicity of a multivalent fluoropeptide vaccine versus its native peptide equivalent in BALB/c and CBF6 mice, after prime or prime-boost, assessed by ex vivo IFN-γ ELIspot assay.

FIG. 2 shows a comparison of the immunogenicity of a multivalent fluoropeptide vaccine versus its native peptide equivalent in BALB/c and CBF6 mice, after prime or prime-boost, assessed by ex vivo IFN-γ ELIspot assay.

FIG. 3 shows a comparison of individual peptide immunogenicity of fluoropeptides verses native peptides in BALB/c and CBF6 mice after prime or prime-boost assessed by ex vivo IFN-γ ELISpot.

FIG. 4 shows a comparison of the immunogenicity of a multivalent fluoropeptide vaccine versus the native peptide equivalent in BALB/c and CBF6 mice after prime-boost immunization, assessed by cytokine profiles.

FIG. 5 is a graph showing that both CD4+ T cells and CD8+ T cells are stimulated by the fluoropeptide vaccine in BALB/c mice.

FIG. 6 shows a comparison of the immunogenicity of a multivalent fluoropeptide vaccine versus vaccine emulsified in CFA in BALB/c mice after a single immunization; assessment of cytokine profiles.

FIG. 7 shows a comparison of subcutaneous versus intradermal routes of fluoropeptide vaccine administration in BALB/c mice after a single immunization: ex vivo IFN-γ ELISpot assay.

DETAILED DESCRIPTION

Over the decades numerous delivery methods have been evaluated, including vectors such as Penetratin, TAT and its derivatives, DNA, viral vectors, virosomes and liposomes. However, these systems either elicit very weak CTL responses, fail to generate a booster amplification on memory responses, have associated toxicity issues or are complicated and expensive to manufacture at the commercial scale. There is therefore a recognised need for improved vectors to direct the intracellular delivery of antigens in the development of vaccines and drugs intended to elicit a cellular immune response. A vector in the context of immunotherapeutics or vaccines is any agent capable of transporting or directing an antigen to immune responsive cells in a host.

The present invention seeks to overcome the problem of delivering influenza antigens to immune responsive cells by using a fluorocarbon vector in order to enhance their immunogenicity. The fluorocarbon vector may comprise one or more chains derived from perfluorocarbon or mixed fluorocarbon/hydrocarbon radicals, and may be saturated or unsaturated, each chain having from 3 to 30 carbon atoms.

Fluorinated surfactants have low critical micelle concentrations and thus self-organise into multimolecular micelle structures at a low concentrations. This physicochemical property is related to the strong hydrophobic interactions and low Van der Waal's interactions associated with fluorinated chains which dramatically increase the tendency of fluorinated amphiphiles to self-assemble in water and to collect at interfaces. The formation of such structures facilitates their endocytic uptake by cells, to for example antigen-presenting cells (Reichel F. et al. J. Am. Chem. Soc. 1999, 121, 7989-7997). Furthermore haemolytic activity is strongly reduced and often suppressed when fluorinated chains are introduced into a surfactant (Riess et al. Adv. Mater. 1991, 3, 249-251) thereby leading to a reduction in cellular toxicity.

In order to link the vector to the antigen through a covalent linkage, a reactive group, or ligand, is incorporated as a component of the vector, for example —CO—, —NH—, S, O or any other suitable group is included; the use of such ligands for achieving covalent linkages are well-known in the art. The reactive group may be located at any position on the fluorocarbon molecule.

Coupling of the fluorocarbon vector to the antigen may be achieved through functional groups such as —OH, —SH, —COOH, —$NH_2$ naturally present or introduced onto any site of the antigen. Suitable links may contain a nitrogen, oxygen or sulphur atom, in either linear or cyclic form. Examples of the bonds formed by ligation may include oxime, hydrazone, disulphide or triazole or any suitable covalent bond. In particular, the fluorocarbon moiety could be introduced through a thioester bond to increase the immunogenicity of the peptide (Beekman et al. "Synthetic peptide vaccines: palmitoylation of peptide antigens by a thioester bond increases immunogenicity." J. Peptide Res. 1997, 50, 357-364). Optionally, a spacer element (peptidic, pseudopeptidic or non-peptidic) may be incorporated to permit cleavage of the antigen from the fluorocarbon element for processing within the antigen-presenting cell and to optimise antigen presentation, as previously shown for lipopeptides (Verheul et al. "Monopalmitic acid-peptide conjugates induce cytotoxic T cell responses against malarial epitopes: importance of spacer amino acids," Journal of Immunological Methods 1995, volume 182, pp 219-226).

In a first aspect, the present invention provides a fluorocarbon vector-antigen construct having a chemical structure $C_mF_{n-}C_yH_x$-(Sp)-R or derivatives thereof, where m=3 to 30, n<=2m+1, y=0 to 15, x<=2y, (m+y)=3-30 and Sp is an optional chemical spacer moiety and R is an antigen derived from the influenza virus.

In the context of the present invention "derivatives" refers to relatively minor modifications of the fluorocarbon compound such that the compound is still capable of delivering the antigen as described herein. Thus, for example, a number of the fluorine moieties can be replaced with other halogen moieties such as chlorine (CO, if) bromine (Br) or iodine (I). In addition it is possible to replace a number of the fluorine moieties with methyl groups and still retain the properties of the molecule as discussed herein.

In a particular example of the above formula the vector may be 2H, 2H, 3H, 3H-perfluoroundecanoic acid of the following formula:

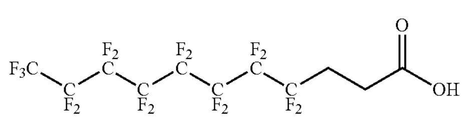

Thus in a second aspect the invention provides a fluorocarbon vector-antigen construct of structure 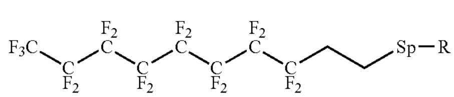 where Sp is an optional chemical spacer moiety and R is an antigen derived from the influenza virus.

As used herein the term "antigen" refers to a molecule having the ability to be recognized by immunological receptors such as T cell receptor (TCR) or B cell receptor (BCR or antibody). Antigens may be proteins, protein subunits, peptides, carbohydrates, lipid or combinations thereof, natural or non-natural, provided they present at least one epitope, for example a T cell and/or a B cell epitope.

Such antigens may be derived by purification from the native protein or produced by recombinant technology or by chemical synthesis. Methods for the preparation of antigens are well-known in the art. Furthermore, antigens also include DNA or oligonucleotide encoding an antigenic peptide or protein.

The antigen associated with the vector may be any influenza antigen capable of inducing an immune response in an animal, including humans. Preferably the immune response will have a beneficial effect in the host.

The influenza antigen may contain one or more T cell epitopes or one or more B cell epitopes or combinations of T and B cell epitopes.

The T cell epitopes may be MHC class I or class II restricted.

As used herein the term "epitope" includes:

(i) CD4+ T cell epitopes which are peptidic sequences containing an MHC class II binding motif and having the ability to be presented at the surface of antigen presenting cells by MHC class II molecules, and (ii) CD8+ T cell epitopes which are peptidic sequences containing an MHC class I binding motifs and having the ability to be presented by MHC class I molecules at the cell surface, and (iii) B cell epitopes which are peptidic sequences having a binding affinity for a B cell receptor.

The antigen may comprise one or more epitopes from an influenza type A protein, an influenza type B protein or an influenza type C protein. Examples of the influenza virus proteins, from both the influenza A and B types, include: haemagglutinin, neuraminidase, matrix (M1) protein, M2, nucleoprotein (NP), PA, PB1, PB2, NS1 or NS2 in any such combination.

Thus in a further aspect, the present invention provides a vector-antigen construct where the influenza virus antigen is a protein, protein subunit, peptide, carbohydrate or lipid or combinations thereof. For the construct to be immunologically active the antigen must comprise one or more epitopes. Preferably the antigen is a peptide sequence derived from the influenza virus. Peptides or proteins of the invention preferably contain a sequence of at least seven, more preferably between 9 and 100 amino-acids and most preferably between around 15 to 40 amino acids. Preferably, the amino acid sequence of the epitope(s) bearing peptide is selected to enhance the solubility of the molecule in aqueous solvents. Furthermore, the terminus of the peptide which does not conjugate to the vector may be altered to promote solubility of the construct via the formation of multi-molecular structures such as micelles, lamellae, tubules or liposomes. For example, a positively charged amino acid could be added to the peptide in order to promote the spontaneous assembly of micelles. Either the N-terminus or the C-terminus of the peptide can be coupled to the vector to create the construct. To facilitate large scale synthesis of the construct, the N- or C-terminal amino acid residues of the peptide can be modified. When the desired peptide is particularly sensitive to cleavage by peptidases, the normal peptide bond can be replaced by a non-cleavable peptide mimetic; such bonds and methods of synthesis are well known in the art.

Non-standard, non-natural amino-acids can also be incorporated in peptide sequences provided that they do not interfere with the ability of the peptide to interact with MHC molecules and remain cross-reactive with T cells recognizing the natural sequences. Non-natural amino-acids can be used to improve peptide resistance to protease or chemical stability. Examples of non-natural amino acids include the D-amino-acids and cysteine modifications.

More than one antigen may be linked together prior to attachment to the fluorocarbon vector. One such example is the use of fusion peptides where a promiscuous T helper epitope can be covalently linked to one or multiple CTL epitopes or one or multiple B cell epitope which can be a peptide, a carbohydrate, or a nucleic acid. As an example, the promiscuous T helper epitope could be the PADRE peptide, tetanus toxoid peptide (830-843) or influenza haemagglutinin, HA (307-319). Alternatively, the peptide sequence may contain two or more epitopes, which may be overlapping thereby creating a cluster of densely packed multi-specific epitopes, or contiguous, or separated by a stretch of amino acids.

Thus in a further aspect, the present invention provides a vector-antigen construct where R is more than one epitope or antigen linked together. Epitopes may also be linear overlapping thereby creating a cluster of densely packed multi-specific epitopes.

Due to the strong non-covalent molecular interactions characteristic to fluorocarbons, the antigen may also be non-covalently associated with the vector and still achieve the aim of being favorably taken up by antigen-presenting cells.

Thus in a further aspect, the present invention provides a vector/antigen construct where the antigen is non-covalently associated with the fluorocarbon vector.

Antigens bearing one or more B-cell epitopes may also be attached to the fluorocarbon vector, either with or without one or more T-cell epitopes. B cell epitopes can be predicted using in silico approaches (Bublil et al. "Stepwise prediction of conformational discontinuous B-cell epitopes using the Mapitope algorithm." Proteins. 2007 Jul. 1; 68(1):294-304. Greenbaum et al. "Towards a consensus on datasets and evaluation metrics for developing B-cell epitope prediction tools" J Mol Recognit. 2007 March-April; 20(2):75-82).

The present invention also provides vaccines and immunotherapeutics comprising one or more fluorocarbon vector-antigen constructs. Multi-component products of this type are desirable since they are likely to be more effective in eliciting appropriate immune responses in a greater number of individuals. Due to extreme HLA polymorphism in humans, it is unlikely that a single fluoropeptide will induce a multiepitopic immune response in a high percentage of a given population. Therefore, in order for a vaccine product to be effective across a population a number of fluoropeptides may be necessary in the vaccine formulation in order to provide broad coverage. Moreover, the optimal formulation of an influenza vaccine or immunotherapeutic may comprise a number of different peptide sequences derived from different influenza virus antigens. In this case the peptides may be linked together attached to a single fluorocarbon vector or each peptide antigen could be bound to a dedicated vector.

A multi-component product may contain one or more vector-antigen constructs, more preferably 2 to about 20, more preferably 3 to about 10. In particular embodiments the multi component vaccine may contain 5, 6, 7 or 8 eight constructs. This ensures that a multi-epitopic T-cell response is generated with a broad population coverage (i.e., addresses HLA diversity). For example, a formulation of multiple fluoropeptides may be composed of influenza A derived peptides alone, influenza B derived peptides alone or influenza C derived peptides alone or combinations of influenza types, most preferably influenza A and B.

In one embodiment the product comprises at least two vector-antigen constructs, the first construct comprising the influenza peptide sequence:

```
                                         (SEQ ID NO: 1)
HMAIIKKYTSGRQEKNPSLRMKWMMAMKYPITADK
``` and the second construct comprising the influenza peptide sequence:

```
                                         (SEQ ID NO: 17)
YITRNQPEWFRNVLSIAPIMFSNKMARLGKGYMFE
```

In a further embodiment the product comprises 8 vector-antigen constructs which comprise the following influenza peptide sequences:

```
Construct 1 -
                                         (SEQ ID NO: 1)
HMAIIKKYTSGRQEKNPSLRMKWMMAMKYPITADK Construct 2 -
                                         (SEQ ID NO: 4)
VAYMLERELVRKTRFLPVAGGTSSVYIEVLHLTQG Construct 3 -
                                         (SEQ ID NO: 17)
YITRNQPEWFRNVLSIAPIMFSNKMARLGKGYMFE Construct 4 -
                                         (SEQ ID NO: 18)
APIMFSNKMARLGKGYMFESKXMKLRTQIPAEMLA, where X can be R or S Construct 5 -
                                         (SEQ ID NO: 19)
SPGMMMGMFNMLSTVLGVSILNLGQKKYTKTTY Construct 6 -
                                         (SEQ ID NO: 20)
KKKSYINKTGTFEFTSFFYRYGFVANFSMELPSFG Construct 7 -
                                         (SEQ ID NO: 32)
DQVRESRNPGNAEIEDLIFLARSALILRGSVAHKS Construct 8 -
                                         (SEQ ID NO: 35)
DLEALMEWLKTRPILSPLTKGILGFVFTLTVPSER
```

Alternatively, multiple epitopes may be incorporated into a formulation in order to confer immunity against a range of pathogens, one of which is the influenza virus. For example a respiratory infection vaccine may contain antigens from influenza virus and respiratory syncytial virus.

Compositions of the invention comprise fluorocarbon vectors associated to antigens optionally together with one or more pharmaceutically acceptable carriers and/or adjuvants. Such adjuvants and/or pharmaceutically acceptable carriers, would be capable of further potentiating the immune response both in terms of magnitude and/or cytokine profile, and may include, but are not limited to:

(1) natural or synthetically derived refinements of natural components of bacteria such as Freund's adjuvant & its derivatives, muramyldipeptide (MDP) derivatives, CpG, monophosphoryl lipid A;
(2) other known adjuvant or potentiating agents such as saponins, aluminium salts and cytokines;
(3) methods of formulating antigens with or without extraneous adjuvants (see 1 & 2 above) such as oil in water adjuvants, water-in-oil adjuvants, immunostimulating complex (ISCOMs), liposomes, formulated nano and micro-particles;
(4) bacterial toxins and toxoids; and
(5) other useful adjuvants well-known to one skilled in the art.

The choice of carrier if required is frequently a function of the route of delivery of the composition. Within this invention, compositions may be formulated for any suitable route and means of administration. Pharmaceutically acceptable carriers or diluents include those used in formulations suitable for oral, ocular, rectal, nasal, topical (including buccal and sublingual), vaginal or parenteral (including subcutaneous, intramuscular, intravenous, intradermal, transdermal) administration.

The formulation may be administered in any suitable form, for example as a liquid, solid, aerosol, or gas. For example, oral formulations may take the form of emulsions, syrups or solutions or tablets or capsules, which may be enterically coated to protect the active component from degradation in the stomach. Nasal formulations may be sprays or solutions. Transdermal formulations may be adapted for their particular delivery system and may comprise patches. Formulations for injection may be solutions or suspensions in distilled water or another pharmaceutically acceptable solvent or suspending agent.

Thus in a further aspect, the present invention provides a prophylactic or therapeutic formulation comprising the vector-antigen construct(s) with or without a suitable carrier and/or adjuvant.

The appropriate dosage of the vaccine or immunotherapeutic to be administered to a patient will be determined in the clinic. However, as a guide, a suitable human dose, which may be dependent upon the preferred route of administration, may be from 1 to 1000 µg. Multiple doses may be required to achieve an immunological or clinical effect, which, if required, will be typically administered between 2 to 12 weeks apart. Where boosting of the immune response over longer periods is required, repeat doses 1 month to 5 years apart may be applied.

The formulation may combine the vector-antigen construct with another active component to effect the administration of more than one vaccine or drug. A synergistic effect may also be observed through the co-administration of the two or more actives.

A vaccine formulation of the invention, comprising one or more fluoropeptides, may be used in combination with a humoral response-based influenza vaccine, such as Fluzone®, Agrippal™, Begrivac™, Fluvax®, Enzira®, Fluarix™, Flulaval™, FluAd®, Influvac®, Fluvirin®, FluBlok® or any influenza vaccine comprising haemagglutinin as the active component, or a live attenuated influenza virus, including the cold-adapted strains such as Flumist®. Administration may be as a combined mixture or as separate vaccine agents administered contemporaneously or separated by time.

In a further aspect the influenza vaccine formulation may be administered in combination with an anti-viral therapeutic composition, including neuraminidase inhibitor treatments such as amanidine, rimantidine, zanamivir or oseltamivir. Administration may be contemporaneous or separated by time.

In other aspects the invention provides:
i) Use of the immunogenic construct as described herein in the preparation of a medicament for treatment or prevention of a disease or symptoms thereof.
ii) A method of treatment through the induction of an immune response following administration of the formulation described herein.

Role of T Cells in Protection Against Influenza Disease

Whilst conventional influenza vaccine technologies have focused primarily on the antibody responses to the viral surface proteins, these are subject to antigenic shift and drift which undermines efficacy and creates the logistical vulnerabilities described. In contrast, T cells, which mediate cellular immune responses, can target proteins more highly conserved across heterologous viral strains and clades. This property gives vaccines that induce protective cellular immune responses the potential to protect against heterologous viral strains and clades (heterosubtypic immunity). For the influenza virus, conservation of the PB1, PB2, PA, NP, M1, M2, NS1 and NS2 proteins and persistence of the corresponding antigen-specific CD4+ and CD8+ T cells makes these proteins attractive vaccine targets.

Protective antiviral cell-mediated immunity consists of the induction of a Type 1 response supported by Type 1 CD4+ T-helper lymphocytes (Th1) leading to the activation of immune effector mechanisms including the induction and maintenance of cytotoxic T lymphocytes (CTLs) as well as immunostimulatory cytokines such as IFN-γ and IL-2. The CD4+ T helper cells are primarily responsible for helping other immune cells through direct cell-cell interactions or by secreting cytokines after recognizing antigenic T cell peptide epitopes bound to major histocompatibility complex (MHC) class II molecules. The cytotoxic T lymphocytes (CTLs) typically express CD8 and induce lysis or apoptosis of cells on which they recognize foreign antigens presented by MHC class I molecules, providing a defense against intracellular pathogens such as viruses. This association of phenotype and function is not absolute, since CD4+ cells may exhibit cytolytic activity, while CD8+ cells secrete antiviral cytokines, notably interferon-γ (IFN-γ) and tumor necrosis factor. Indeed, CD4$^+$ CTL activity has been proposed as another immune mechanism to control acute and chronic viral infection in humans. CD4$^+$ CTL may control viral spread by direct antiviral cytolytic effect and may play a direct antiviral activity by the production of antiviral cytokines such as IFN-γ. IFN-γ is known to have a direct inhibitory and non-cytolytic effect on virus production. CD4+ T helper cells are also essential in determining B cell antibody response and class switching, and in maximizing bactericidal activity of phagocytes such as macrophages.

Cellular immune responses are believed to play an important role in controlling influenza infection, ameliorating signs of disease and promoting disease recovery. Influenza-specific cellular immunity is elicited following natural infection and several viral proteins have been identified as targets for human memory heterosubtypic T cell responses, including nucleoprotein (NP), polymerase (PB1, PB2, & PA), M1 and M2 proteins, and non-structural protein-1 (NS1). NS2 may also be implicated. These internal proteins contain highly conserved and immunodominant regions making them ideal T cell targets. In particular, experimental studies have shown that influenza-A NP represents an important target antigen for both subtype-specific and cross-reactive CTLs in mice and humans. This contrasts with haemagglutinin (HA) and neuraminidase (NA), which are unsuitable targets due to their high sequence variability within and between influenza subtypes.

More specifically, cell-mediated immunity is strongly implicated in the protection against influenza disease including highly pathogenic strains. Memory CD4+ and CD8+ T cells are present in the lung airways and evidence is mounting that these cells play a role in pulmonary immunity to influenza challenge by mediating engagement of the pathogen at the site of infection when pathogen loads are low. Depletion of CD8+ T cells reduces the capacity of primed mice to respond to influenza infection, which signifies a role for CD8+ T cells in the protective secondary response. Because viral replication is confined to cells in the respiratory epithelium, CD8+ T cells exert their effector functions at this site, producing antiviral cytokines and lysing target cells presenting viral determinants for which they bear a specific T-cell receptor. Lysis of infected epithelial cells is mediated by exocytosis granules containing perforin and granzyme, as well as Fas mechanisms. (Thomas et al. "Cell-mediated protection in influenza infection." Emerg Infect Dis. 2006 January; 12(1):48-54).

Vigorous CD4+ T cell responses to influenza are initiated in the draining lymph node followed by the spleen and they peak in the lung and bronchoalveolar secretions at day 6-7 post infection. This primary CD4 T-cell response to influenza infection, albeit smaller in magnitude than the CD8 response, has been shown to involve robust CD4+ expansion, Th-1 differentiation and their migration to the site of infection. CD4+ T-helper cells are also necessary for long lasting and effective CD8 memory to influenza infection. CD4 effector T-cell and memory responses contribute to immunity against influenza via multiple mechanisms including their classic contribution as helpers during the generation of influenza specific CD8+ CTL responses, their ability to drive IgG2a to neutralize infective viral particles, and via their direct antiviral activity through the secretion of IFN-gamma. Both CD4+ and CD8+ T-cell epitopes have been shown to promote viral clearance and confer protection in mice against an influenza challenge.

Mouse models for influenza-A virus provide an experimental system to analyze T-cell mediated immunity. In particular, the T-cell immune response to influenza infection has been well characterized in C57BL/6 (H2$^b$) and Balb/C (H2$^d$) mice and their hybrids. Plotnicky et al. "The immunodominant influenza matrix T cell epitope recognized in human induces influenza protection in HLA-A2/K(b) transgenic mice." Virology. 2003 May 10; 309(2):320-9.) demonstrated the protective efficacy of the influenza matrix protein (M1) epitope 58-66 to lethal transgenic murine challenge. Protection was mediated by T-cells since protection was abolished following in vivo depletion of CD8+ and/or CD4+ T-cells. Mouse survival correlated with M1-specific T-cells in the lungs, which were directly cytotoxic to influenza-infected cells following influenza challenge. Woodland et al. "Identification of protective and non-protective T cell epitopes in influenza." Vaccine. 2006 Jan. 23; 24(4):452-6) also demonstrated that a single CD4+ T cell epitope HA (211-225) could confer partial control of viral infection in vaccinated mice.

Whilst T cell targets tend to be prone to less frequent mutation than the influenza virus surface protein B cell epitopes, CD8+ and CD4+ T cell epitopes will also mutate under protective immune pressure over time (Berkhoff et al. "Fitness costs limit escape from cytotoxic T lymphocytes by influenza A viruses." Vaccine. 2006 Nov. 10; 24(44-46): 6594-6.). This escape likely results from the confrontation between the virus and the highly polymorphic human leukocyte antigen (HLA) class I and II proteins which determines antigen processing and epitope presentation to host CD8$^+$ and CD4+ T-cells respectively. This viral escape mechanism has been more clearly established for HIV and HCV and is known to shape the evolution of the virus. Therefore the selection of highly conserved peptide sequences with low inherent variability (entropy) is an important factor to be considered in the design of T-cell vaccines which can specifically counter antigenic shift and drift. Such methods have been described by Berkhoff et al. "Functional constraints of influenza A virus epitopes limit escape from cytotoxic T lymphocytes" J Virol. 2005 September; 79(17):11239-46.)

Adults over 65 years of age currently account for approximately 90% of all influenza-related mortality. This is also the target group where current vaccines are least effective. In humans, ageing appears to be associated with a decline in the ability to generate T-cell effectors from memory subpopulations. An increased frequency of central memory CD4+ T-cells and decreased frequency of effector memory CD4+ T cells in the elderly post-vaccination has been observed, which may be related to decreased levels of serum IL-7. Elderly subjects also demonstrate a blunted type-1 T-cell response to influenza vaccination which correlates directly with IgG1 responses. Furthermore, mice also exhibit an age related impairment of epitope-specific CD8+ CTL activity during primary influenza-A infection. This is associated with a defect in expansion of CD8+ CTL rather than effector activity of influenza-specific CD8+ T cells. (Mbawuike et al. "Reversal of age-related deficient influenza virus-specific CTL responses and IFN-gamma production by monophosphoryl lipid A." Cell Immunol. 1996 Oct. 10; 173(1):64-78.)

As an important element of the T cell response is directed at the clearance of infected cells, a T-cell vaccine may be used in a prophylactic manner to generate memory recall as well as in a therapeutic mode, post-infection, to enhance the host's natural cell-mediated immunity. The T-cell vaccine may also be used in combination with a conventional antibody-generating (humoral response-based) influenza vaccine, either through co-administration or by separate administration.

T-Cell Vaccine Approaches

A review of the T-cell and Influenza vaccine fields highlights a number of critical challenges faced in the design of a broadly cross protective T-cell vaccine. A T-cell vaccine must first be capable of priming and boosting CD4+ HTL and CD8+ CTL T-cell memory and effector functions in a high percentage of vaccine recipients. Such a vaccine must also address viral genetic diversity, and ongoing mutation, as well as human genetic diversity manifest at the level of MHC allele polymorphism. The proposed invention seeks to address these design issues by combining a novel fluoropeptide vaccine delivery system together with highly conserved influenza peptides. The peptides are preferably antigens known to contain one or more epitopes, in particular T-cell epitopes.

Traditional peptide-based T-cell vaccine approaches have been epitope-based and focussed on minimal CTL (8-11aa) or T-helper (13aa) epitopes delivered as single epitopes or reconstituted artificial strings. Non-natural sequences may face inefficient antigen processing constraints as well as giving rise to the potential formation of unrelated neo-epitopes. Long, natural conserved peptide sequences containing overlapping T-cell epitopes, clustered T-cell epitopes or promiscuous T-cell epitopes in a single peptide sequence permit natural antigen processing while achieving broad population coverage. Moreover, the use of multiples of these long natural peptides in the one vaccine formulation is likely to offer even greater population coverage. Precedent shows long peptides (30-35aa) comprising CD4+& CD8+ T-cell epitopes have the ability to induce multi-epitopic responses in animals and humans (Coutsinos et al. "Long-term specific immune responses induced in humans by a human immunodeficiency virus type 1 lipopeptide vaccine: characterization of CD8+-T-cell epitopes recognized." J Virol. 2003 October; 77(20):11220-31.). For an effective anti-viral CTL response (CD8 T cell driven), an appropriate Th-1 cytokine environment is required (ensured by CD4 cells), thus the concomitant delivery of CD4 and CD8 epitopes is predicted to enhance cellular responses (Krowka et al. "A requirement for physical linkage between determinants recognized by helper molecules and cytotoxic T cell precursors in the induction of cytotoxic T cell responses" J. Immunol 1986, May 15; 136(10):3561-6.).

CD4+ and CD8+ T cells recognize short peptides resulting from the extracellular and intracellular processing of foreign and self proteins, presented bound to specific cell surface molecules encoded by the MHC system. There are two discrete classes of MHC molecules: (i) MHC class I presents endogenous peptides; and (ii) MHC class II presents exogenous peptides. The process of MHC class I antigen presentation involves protein degradation, peptide transport to the endoplasmic reticulum, peptide-MHC binding and export of peptide-MHC complexes to the cell surface for recognition by CD8+ T cells. Peptides are bound within a specific MHC binding groove, the shape and characteristics of which results in the binding of specific subsets of peptides sharing a common binding motif T cells are activated when the T-cell receptor recognizes a specific peptide-MHC complex, and in this way identify cells infected by intracellular parasites or viruses or cells containing abnormal proteins (e.g. tumor cells) and mount appropriate immune responses against them.

The peptides involved in specific peptide-MHC complexes triggering T-cell recognition (T-cell epitopes) are important tools for the diagnosis and treatment of infectious, autoimmune, allergic and neoplastic diseases. Because T-cell epitopes are subsets of MHC-binding peptides, precise identification of portions of proteins that can bind MHC molecules is important for the design of vaccines and immunotherapeutics. The MHC polymorphism is very high in the human population with 580 HLA-A, 921 HLA-B, 312 HLA-C, 527 HLA-DR(beta), 127 HLA-DRQ(beta) and 86 HLA-DQ(beta) alleles known to date. This situation is challenging when having to design a T-cell based vaccine with broad population coverage. MHC-binding peptides contain position-specific amino acids that interact with the groove of the MHC molecule(s), contributing to peptide binding. The preferred amino acids at each position of the binding motif may vary between allelic variants of MHC molecules. Computational models facilitate identification of peptides that bind various MHC molecules. A variety of computational methods, MHC binding assays, X-ray crystallography study and numerous other methods known in the art permit the identification of peptides that bind to MHC molecules. Novel in silico antigen identification methodologies offer the ability to rapidly process the large amounts of data involved in screening peptide sequences for HLA binding motifs necessary to delineate viral sequences useful for a T cell vaccine. HLA based bioinformatics approaches have been successfully applied in many fields of immunology and make it possible to address human genetic diversity concerns, for example: Depil et al. "Determination of a HLA II promiscuous peptide cocktail as potential vaccine against EBV latency II malignancies.", J Immunother (1997). 2007 February-March; 30(2):215-26; Frahm et al. "Extensive HLA class I allele promiscuity among viral CTL epitopes." Eur J Immunol. 2007 Aug. 17; 37(9):2419-2433; Schulze zur Wiesch et al. "Broad repertoire of the CD4+ Th cell response in spontaneously controlled Hepatitis C virus infection includes dominant and highly promiscuous epitopes." J Immunol. 2005 Sep. 15; 175(6):3603-13; Doolan et al. "HLA-DR-promiscuous T cell epitopes from *Plasmodium falciparum* pre-erythrocytic-stage antigens restricted by multiple HLA class II alleles." J Immunol. 2000 Jul. 15; 165(2):1123-37.).

Peptides that bind more than one MHC allelic variant ('promiscuous peptides') are prime targets for vaccine and immunotherapy development because they are relevant to a greater proportion of the human population. Promiscuous CD4+ T cell epitopes were also reported to bind multiple MHC class II molecules. (Panina-Bordignon et al. "Universally immunogenic T cell epitopes: promiscuous binding to human MHC class II and promiscuous recognition by T cells." Eur J Immunol. 1989 December; 19(12):2237-42.) On the other hand, some promiscuous CD8+ T cell epitopes were previously described having the ability to bind multiples MHC class I molecules sharing binding characteristics and forming a so-called supertype (Frahm et al. "Extensive HLA class I allele promiscuity among viral CTL epitopes." Eur J Immunol. 2007 Aug. 17; 37(9):2419-2433; Sette et al. 'HLA supertypes and supermotifs: a functional perspective on HLA polymorphism.' Curr Opin Immunol. 1998 August; 10(4):478-82). The identification of promiscuous CD4+ and CD8+ T cell epitopes represent an important strategy in vaccine design in order to achieve broad population coverage. MHC polymorphism is also addressed by selecting peptides known or predicted to contain an MHC binding motif related to highly frequent MHC alleles in a specific ethnic group or across multiple ethnic groups.

By selecting a combination of sequences that provide broad population coverage and are conserved across a range of influenza strains (identified by using, for example, the National Center for Biotechnology Information (NCBI) or Los Alamos National Laboratory (LANL) influenza sequence databases) one is able to address viral genetic diversity and achieve protection against the majority, if not all, relevant influenza strains.

Historically, the key failings of T-cell vaccine technologies (DNA and viral vector vaccines) have been the low percentage of vaccine subjects responding to the vaccines, often low levels of immunogenicity and their ability to achieve a booster amplification of memory and effector T-cell responses. The principal goal for an effective influenza T-cell vaccine is to promote robust T-cell memory responses such that on re-exposure to antigen there is rapid expansion of effector functions which control viral load and promote viral clearance from the lungs. To achieve this, robust virus specific Th-1 directed CD4+& CD8+ T-cell central and effector memory responses are required. For a viable, commercial product this response must be elicited in a high percentage of vaccine recipients (>90%) and be capable of generating long term memory responses which will be required for memory recall and subsequent disease protection post-infection. However, to generate this type of durable immunity a vaccine must also achieve a robust booster amplifying effect with repeat vaccine exposure.

Current immunological strategies to improve the cellular immunity induced by vaccines and immunotherapeutics include the development of live attenuated versions of the pathogen and the use of live vectors to deliver appropriate antigens or DNA coding for such antigens. Such approaches, which invariably fail to generate a meaningful booster response in unselected populations, have led to convoluted prime-boost combinations and are also limited by safety considerations within an increasingly stringent regulatory environment. In addition, issues arising from the scalability of manufacturing processes and prohibitive costs often limit the commercial viability of products of biological origin. In this context, synthetic peptides are very attractive antigens as they are chemically well-defined, highly stable and can be designed to contain T and/or B cell epitopes.

In order to stimulate T lymphocyte responses in vivo, synthetic peptides contained in a vaccine or an immunotherapeutic product should preferably be internalized by antigen presenting cells and especially dendritic cells. Dendritic cells (DCs) play a crucial role in the initiation of primary T-cell mediated immune responses. These cells exist in two major stages of maturation associated with different functions. Immature dendritic cells (iDCs) are located in most tissues or in the circulation and are recruited into inflamed sites in the body. They are highly specialised antigen-capturing cells, expressing large amounts of receptors involved in antigen uptake and phagocytosis. Following antigen capture and processing, iDCs move to local T-cell locations in the lymph nodes or spleen. During this process, DCs lose their antigen-capturing capacity turning into immunostimulatory mature DCs (mDCs).

Dendritic cells are efficient presenting cells that initiate the host's immune response to peptide antigen associated with class I and class II MHC molecules. They are able to prime naïve CD4 and CD8 T-cells. According to current models of antigen processing and presentation pathways, exogeneous antigens are internalised into the endocytic compartments of antigen presenting cells where they are degraded into peptides, some of which bind to MHC class II molecules. The mature MHC class II/peptide complexes are then transported to the cell surface for presentation to CD4 T-lymphocytes. In contrast, endogenous antigen is degraded in the cytoplasm by the action of the proteosome before being transported into the cytoplasm where they bind to nascent MHC class I molecules. Stable MHC class I molecules complexed to peptides are then transported to the cell surface to stimulate CD8 CTL. Exogenous antigen may also be presented on MHC class I molecules by professional APCs in a process called cross-presentation. Phagosomes containing extracellular antigen may fuse with reticulum endoplasmic and antigen may gain the machinery necessary to load peptide onto MHC class I molecules The Examples herein highlight the differential T-cell immune response obtained by the attachment of a fluorocarbon vector to antigens compared to the corresponding non-fluorinated antigens. The eight (8) antigens exemplified were selected from the list of Influenza sequences herein defined. This provisional selection utilized a proprietary selection algorithm encompassing a combination of parameters including; immunoinformatics selection, in-vitro binding assays, ex-vivo restimulation assays using human PBMC previously infected with influenza, manufacturing and formulation parameters. Finally the assessment in mice confirmed that fluoropeptides thus selected either individually or in combination were immunogenic and the responses obtained were superior to the native peptide antigens. The antigen selection focus and desire to utilize a combination of antigens for this vaccine prototype is such that both viral genetic and human HLA diversity are addressed in this rational vaccine design. This has been one of the key failings in the peptide vaccine field. Whilst it is possible to utilize a single antigen in the fluoropeptide vaccine it would limit the vaccine's immunogenicity potential in an outbred human (or other) population and therefore the selection of multiple peptides is essential for a broadly effective vaccine.

As used herein (e.g., in the figures) the term "fluoropepetides" refers to fluorocarbon vectors (chains) conjugated to peptide based antigens. The Examples refer to the figures in which:

FIG. 1 shows a comparison of the immunogenicity of a multivalent fluoropeptide vaccine versus its native peptide equivalent in BALB/c and CBF6 mice, after prime or prime-boost, assessed by ex vivo IFN-γ ELIspot assay. Seven or eight mice per group were immunized subcutaneously with the fluoropeptide vaccine (composed of 8 formulated fluoropeptides at a dose of 1 nmol per fluoropeptide in 100 μl) or the equivalent native peptides (composed of 8 formulated native peptides at a dose of 1 nmol per peptide in 100 μl). The control group received a formulation containing excipient only. Ten days after the final injection mice were sacrificed by cervical dislocation. Spleens were removed and single spleen cell suspensions were prepared from individual mice. Murine IFN-γ ELISpot assays (Mabtech, Sweden) were performed according to manufacturer's instructions. Spleen cells ($5\times10^5$) were stimulated, in duplicate, with 8 individual native peptides at a concentration of 10 μg/ml per peptide in complete culture medium (RPMI supplemented with 10% Foetal Calf Serum) in a total volume of 200 μl for 18 hours at 37° C. and 5% $CO_2$. The spots were counted using a CTL-immunospot reader unit. For each mouse, the ft) total number of spots was cumulated for all 8 peptides and the value of the control wells (media only) was subtracted 8 times. The results correspond to mean±standard deviation of spot forming cells (SFC) per million input spleen cells.

FIG. 2 shows a comparison of the immunogenicity of a multivalent fluoropeptide vaccine versus its native peptide equivalent in BALB/c and CBF6 mice, after prime or prime-boost, assessed by ex vivo IFN-γ ELIspot assay. Seven or eight mice per group were immunized subcutaneously with the fluoropeptide vaccine (composed of 8 formulated fluoropeptides at a dose of 1 nmol per fluoropeptide in 100 μl) or the equivalent native peptides (composed of 8 formulated native peptides at a dose of 1 nmol per peptide in 100 μl). The control group received a formulation containing excipient only. Ten days after the final injection mice were sacrificed by cervical dislocation. Spleens were removed and single spleen cell suspensions were prepared from individual mice. Murine IFN-γ ELISpot assays (Mabtech, Sweden) were performed according to manufacturer's instructions. Spleen cells ($5\times10^5$) were stimulated, in duplicate, with a mixture of 8 peptides at a concentration of 1 μg/ml per peptide in complete culture medium (RPMI supplemented with 10% Foetal Calf Serum) in a total volume of 200 μl for 18 hours at 37° C. and 5% $CO_2$. The spots were counted using a CTL-immunospot reader unit. For each mouse, the total number of spots was cumulated for all 8 peptides and the value of the control wells (media only) was subtracted 8 times. The results correspond to mean±standard deviation of spot forming cells (SFC) per million input spleen cells.

FIG. 3 shows a comparison of individual peptide immunogenicity of fluoropeptides verses native peptides in BALB/c and CBF6 mice after prime or prime-boost assessed by ex vivo IFN-γ ELISpot. Seven or eight mice per group were immunized subcutaneously with the fluoropeptide vaccine (composed of 8 formulated fluoropeptides at a dose of 1 nmol per fluoropeptide in 100 μl) or the equivalent native peptides (composed of 8 formulated native peptides at a dose of 1 nmol per peptide in 100 μl). The control group received a formulation containing excipient only. Ten days after the last injection mice were sacrificed by cervical dislocation. Spleens were removed and single spleen cell suspensions were prepared from individual mice. Murine IFN-γ ELISpot assays (Mabtech, Sweden) were performed according to manufacturer's instructions. Spleen cells ($5\times10^5$) were stimulated, in duplicate, with 8 individual native peptides at a concentration of 10 μg/ml per peptide in complete culture medium (RPMI supplemented with 10%

Foetal Calf Serum) in a total volume of 200 μl for 18 hours at 37° C. under 5% $CO_2$ atmosphere. The spots were counted using a CTL-immunospot reader unit. The results correspond to mean±standard deviation of spot forming cells (SFC) per million input spleen cells.

Figure 4:
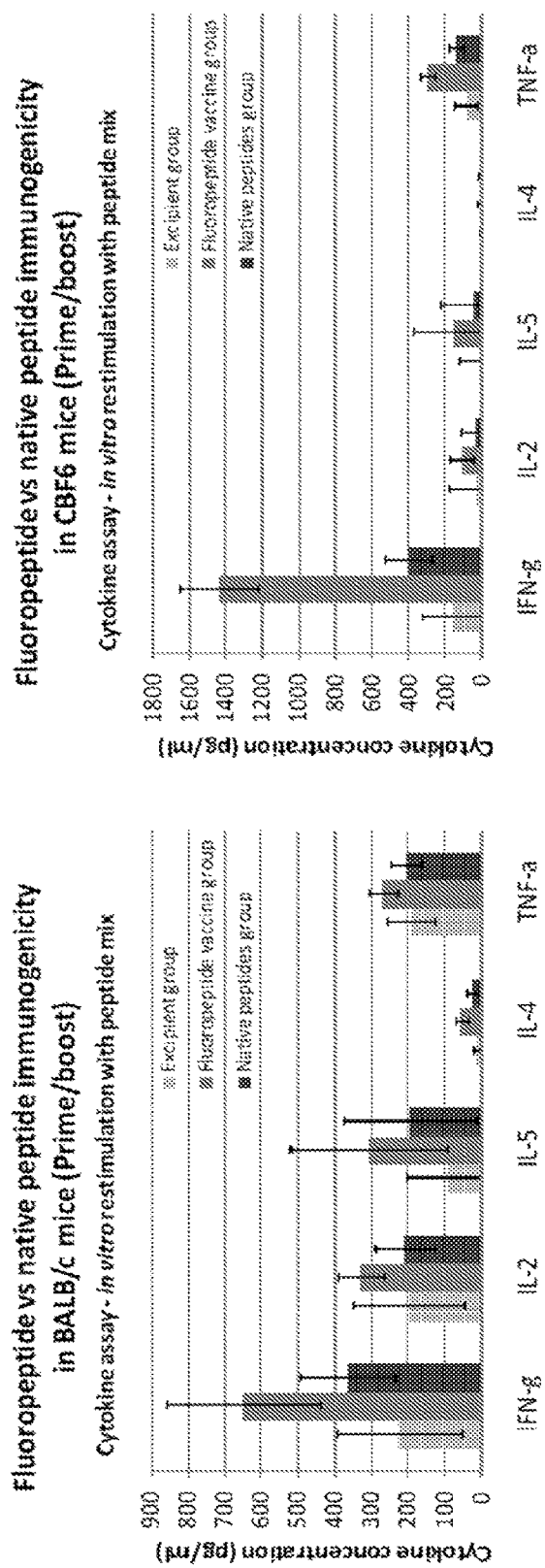

FIG. 4 shows a comparison of the immunogenicity of a multivalent fluoropeptide vaccine versus its native peptide equivalent in BALB/c and CBF6 mice after prime-boost immunization; assessment of cytokine profiles. Eight mice per group were immunized subcutaneously with the fluoropeptide vaccine (composed of 8 formulated fluoropeptides at a dose of 1 nmol per fluoropeptide in 100 μl) or the equivalent native peptides (composed of 8 formulated native peptides at a dose of 1 nmol per peptide in 100 μl). The control groups of mice were injected with a formulation containing excipient only. Mice were immunized at a 15 day interval. Ten days after the last injection mice were sacrificed by cervical dislocation. Spleens were removed and single spleen cell suspensions were prepared from individual mice. Splenocytes were stimulated with a mixture of 8 native peptides at a concentration of 1 μg/ml per peptide in complete culture medium (RPMI supplemented with 10% Foetal Calf Serum) in a total volume of 200 μl for 48 hours at 37° C. under 5% $CO_2$ atmosphere. Analysis of cytokine concentrations (interleukin-2 (IL-2), interleukin-4 (IL-4), interleukin-5 (IL-5), interferon-γ (IFN-γ), and Tumor Necrosis Factor (TNF)) from the culture supernatants of stimulated cells was conducted using a murine cytometric bead array kit (CBA; BD Biosciences, UK) according to manufacturer's instructions and was analyzed using a FacsCanto II flow cytometer. Standard curves were determined for each cytokine from a range of 210-2500 pg/ml. The lower limit of detection for the CBA, according to the manufacturer, is 2.5-3.2 pg/ml, depending on the analyte. The results correspond to mean values and standard deviation calculated for each group of mice for each cytokine. Results are expressed as cytokine concentration in pg/ml.

Figure 5:
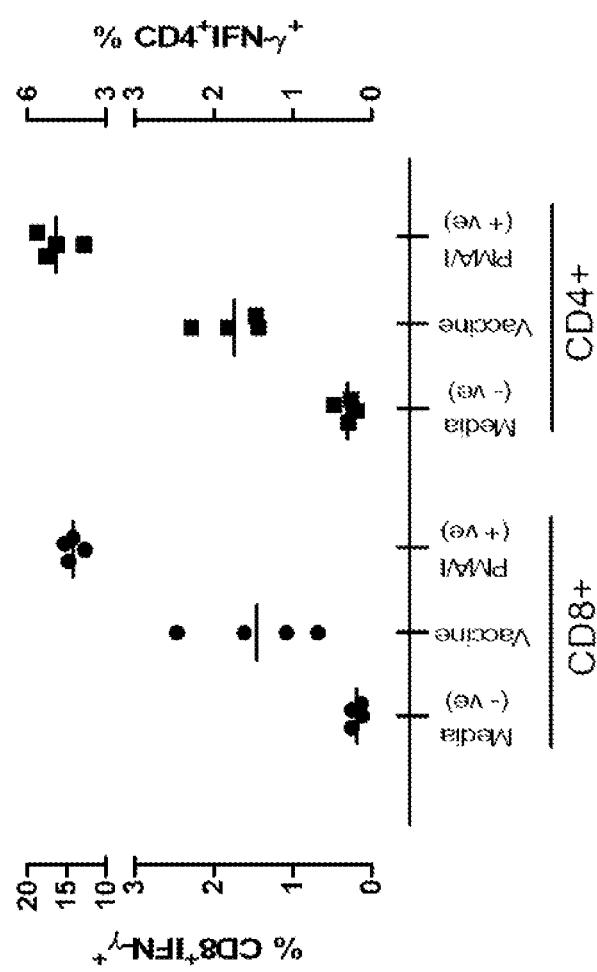

FIG. 5 is a graph showing that both CD4+ T cells and CD8+ T cells are stimulated by the fluoropeptide vaccine in BALB/c mice. Four mice per group were immunized subcutaneously with the fluoropeptide vaccine (composed of 8 formulated fluoropeptides at a dose of 1 nmol per fluoropeptide in 100 μl). Mice received 2 injections (prime-boost) at a 15 day interval. Ten days after the last injection, mice were sacrificed by cervical dislocation. Spleens were removed and single spleen cell suspensions were prepared from individual mice. Cells were resuspended at $0.5 \times 10^6$/well and stimulated with media only or a mixture of 8 native peptides (vaccine) for 72 hours at 37° C. and 5% $CO_2$. Positive control cultures (PMA/I) received 50 ng/ml PMA and 0.5 μg/ml ionomycin for the final 5 hours of culture. All cultures received 10 μl/ml Brefeldin A for the final 5 hours of culture. Cells were stained extracellularly for CD4 and CD8, and intracellularly for IFN-γ, and analyzed by flow cytometry using a BD FACSCanto II cytometer. Results for individual mice are shown as percentage of CD4+ or CD8+ T cells expressing intracellular IFN-γ.

Figure 6:
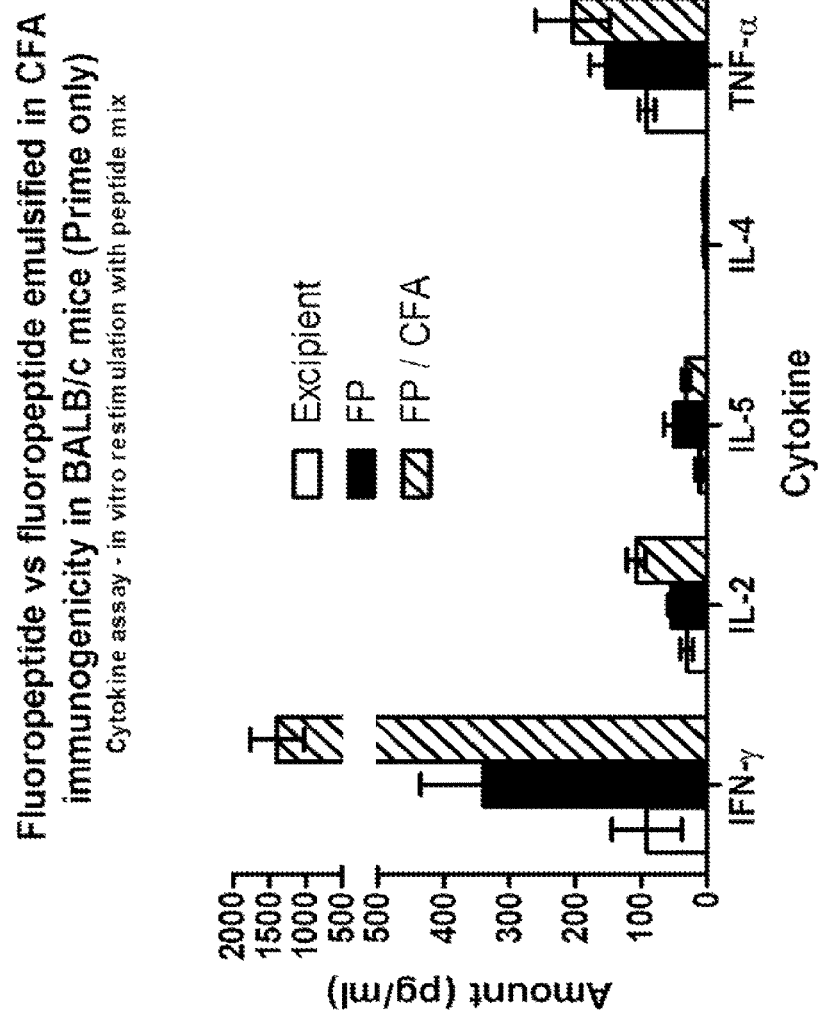

FIG. 6 shows a comparison of the immunogenicity of a multivalent fluoropeptide vaccine versus vaccine emulsified in CFA in BALB/c mice after a single immunization; assessment of cytokine profiles. Ten mice per group were immunized subcutaneously with the fluoropeptide vaccine (composed of 8 formulated fluoropeptides at a dose of 1 nmol per fluoropeptide in 100 μl) or fluoropeptide vaccine emulsified in complete Freund's adjuvant (CFA). The control group of mice was injected with a formulation containing excipient only. Ten days later mice were sacrificed by cervical dislocation. Spleens were removed and single spleen cell suspensions were prepared from individual mice. Splenocytes were stimulated with a mixture of 8 native peptides at a concentration of 1 μg/ml per peptide in complete culture medium (RPMI supplemented with 10% Foetal Calf Serum) in a total volume of 200 μl for 48 hours at 37° C. under 5% $CO_2$ atmosphere. Analysis of cytokine concentrations (interleukin-2 (IL-2), interleukin-4 (IL-4), interleukin-5 (IL-5), interferon-γ (IFN-γ), and Tumor Necrosis Factor (TNF)) from the culture supernatants of stimulated cells was conducted using a murine cytometric bead array kit (CBA; BD Biosciences, UK) according to manufacturer's instructions and was analyzed using a FacsCanto II flow cytometer. Standard curves were determined for each cytokine from a range of 2.5-2500 pg/ml. The lower limit of detection for the CBA, according to the manufacturer, is 2.5-3.2 pg/ml, depending on the analyte. The results correspond to mean values±standard error calculated for each group of mice for each cytokine. Results are expressed as mean cytokine concentration in pg/ml.

Figure 7:
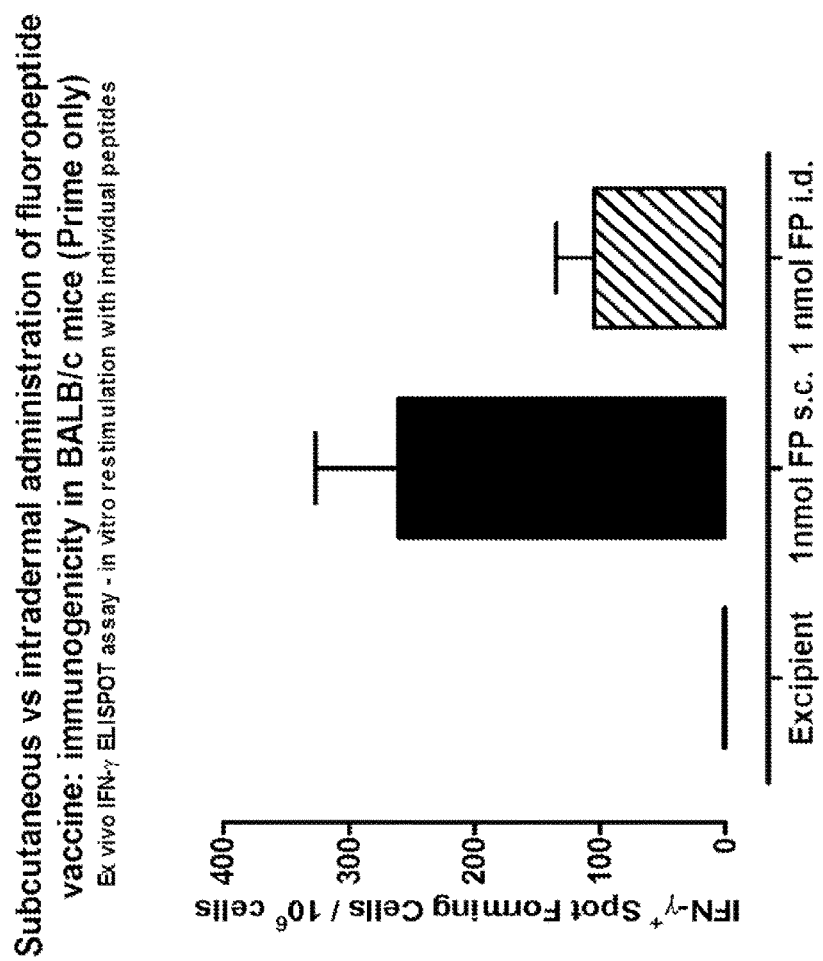

FIG. 7 shows a comparison of subcutaneous versus intradermal routes of fluoropeptide vaccine administration in BALB/c mice after a single immunization: ex vivo IFN-γ ELISpot assay. Ten mice per group were immunized subcutaneously (s.c.) or intradermally (i.d.) with the fluoropeptide vaccine (composed of 8 formulated fluoropeptides at a dose of 1 nmol per fluoropeptide in 100 μl). The control group received a formulation containing excipient only administered subcutaneously. Ten days later mice were sacrificed by cervical dislocation. Spleens were removed and single spleen cell suspensions were prepared from individual mice. Murine IFN-γ ELISpot assays (Mabtech, Sweden) were performed according to manufacturer's instructions. Spleen cells ($5 \times 10^5$) were stimulated, in duplicate, with 8 individual native peptides at a concentration of 10 μg/ml per peptide in complete culture medium (RPMI supplemented with 10% Foetal Calf Serum) in a total volume of 200 μl for 18 hours at 37° C. under 5% $CO_2$ atmosphere. The spots were counted using a CTL-immunospot reader unit. For each mouse, the total number of spots was cumulated for all 8 peptides and the value of the control wells (media only) was subtracted 8 times. The results correspond to mean±standard error of spot forming cells (SFC) per million input spleen cells.

In light of the foregoing description, the specific non-limiting examples presented below are for illustrative purposes and not intended to limit the scope of the invention in any way.

EXAMPLES

Example 1

Example Peptides

Candidates for conjugating to a fluorocarbon vector for inclusion into a prophylactic or therapeutic vaccine for influenza may include the following one or more peptides or fragments thereof, or homologues (including the corresponding consensus, ancestral or central tree sequences as referred to in the Los Alamos National Laboratory influenza sequence database (Macken, C., Lu, H., Goodman, J., & Boykin, L., "The value of a database in surveillance and vaccine selection." in *Options for the Control of Influenza IV*. A. D. M. E. Osterhaus, N. Cox & A. W. Hampson (Eds.) 2001, 103-106.) or Influenza virus resources at NCBI) or natural and non-natural variants thereof, but not necessarily exclusively. Specific examples of appropriate peptides are given below where the standard one letter code has been utilized. Homologues have at least a 50% identity compared to a reference sequence. Preferably a homologue has 80, 85, 90, 95, 98 or 99% identity to a naturally occurring sequence. The use of non-natural amino acids must not interfere with the ability of the peptide to bind to MHC class I or II receptors. Fragments of these sequences that contain one or more epitopes are also candidate peptides for attachment to the fluorocarbon vector.

These sequences were selected from Influenza A consensus sequences. The influenza virus protein and the position of the peptide within that protein are specified. Protein sequences were collected from the Influenza virus resource web site, at ncbi.nlm.nih.gov/genomes/FLU/.

```
                                             SEQ ID No 1
PB2 Position 027 to 061
HMAIIKKYTSGRQEKNPSLRMKWMMAMKYPITADK (SEQ ID NO: 1)

SEQ ID No 2
PB2 Position 123 to 157
ERLKHGTFGPVHFRNQVKIRRRVDINPGHADLSAK (SEQ ID NO: 2)

SEQ ID No 3
PB2 Position 155 to 189
SAKEAQDVIMEVVFPNEVGARILTSESQLTITKEK (SEQ ID NO: 3)

SEQ ID No 4
PB2 Position 203 to 237
VAYMLERELVRKTRFLPVAGGTSSVYIEVLHLTQG (SEQ ID NO: 4)

SEQ ID No 5
PB2 Position 249 to 283
EVRNDDVDQSLIIAARNIVRRAAVSADPLASLLEM (SEQ ID NO: 5)

SEQ ID No 6
PB2 Position 358 to 392
EGYEEFTMVGRRATAILRKATRRLIQLIVSGRDEQ (SEQ ID NO: 6)

SEQ ID No 7
PB2 Position 370 to 404
ATAILRKATRRLIQLIVSGRDEQSIAEAIIVAMVF (SEQ ID NO: 7)

SEQ ID No 8
PB2 Position 415 to 449
RGDLNFVNRANQRLNPMHQLLRHFQKDAKVLFQNW (SEQ ID NO: 8)

SEQ ID No 9
PB2 Position 532 to 566
SSSMMWEINGPESVLVNTYQWIIRNWETVKIQWSQ (SEQ ID NO: 9)

SEQ ID No 10
PB2 Position 592 to 626
YSGFVRTLFQQMRDVLGTFDTVQIIKLLPFAAAPP (SEQ ID NO:
10)

SEQ ID No 11
PB2 Position 607 to 641
LGTFDTVQIIKLLPFAAAPPEQSRMQFSSLTVNVR (SEQ ID NO:
11)

SEQ ID No 12
PB2 Position 627 to 659
QSRMQFSSLTVNVRGSGMRILVRGNSPVFNYNK (SEQ ID NO: 12)

SEQ ID No 13
PB1 Position 012 to 046
VPAQNAISTTFPYTGDPPYSHGTGTGYTMDTVNRT (SEQ ID NO:
13)

SEQ ID No 14
PB1 Position 114 to 148
VQQTRVDKLTQGRQTYDWTLNRNQPAATALANTIE (SEQ ID NO:
14)

SEQ ID No 15
PB1 Position 216 to 250
SYLIRALTLNTMTKDAERGKLKRRAIATPGMQIRG (SEQ ID NO:
15)

SEQ ID No 16
PB1 Position 267 to 301
EQSGLPVGGNEKKAKLANVVRKMMTNSQDTELSFT (SEQ ID NO:
16)

SEQ ID No 17
PB1 Position 324 to 358
YITRNQPEWFRNVLSIAPIMFSNKMARLGKGYMFE (SEQ ID NO:
17)

SEQ ID No 18
PB1 Position 340 to 374
APIMFSNKMARLGKGYMFESKXMKLRTQIPAEMLA (SEQ ID NO:
18)

SEQ ID No 19
PB1 Position 404 to 436
SPGMMMGMFNMLSTVLGVSILNLGQKKYTKTTY (SEQ ID NO: 19)

SEQ ID No 20
PB1 Position 479 to 513
KKKSYINKTGTFEFTSFFYRYGFVANFSMELPSFG (SEQ ID NO:
20)

SEQ ID No 21
PB1 Position 486 to 520
KTGTFEFTSFFYRYGFVANFSMELPSFGVSGINES (SEQ ID NO:
21)

SEQ ID No 22
PB1 Position 526 to 560
GVTVIKNNMINNDLGPATAQMALQLFIKDYRYTYR (SEQ ID NO:
22)

SEQ ID No 23
PB1 Position 656 to 690
EYDAVATTHSWIPKRNRSILNTSQRGILEDEQMYQ (SEQ ID NO:
23)

SEQ ID No 24
PB1 Position 700 to 734
FPSSSYRRPVGISSMVEAMVSRARIDARIDFESGR (SEQ ID NO:
24)

SEQ ID No 25
PA Position 107 to 141
PDLYDYKENRFIEIGVTRREVHIYYLEKANKIKSE (SEQ ID NO:
25)

SEQ ID No 26
PA Position 122 to 156
VTRREVHIYYLEKANKIKSEKTHIHIFSFTGEEMA (SEQ ID NO:
26)

SEQ ID No 27
PA Position 145 to 179
IHIFSFTGEEMATKADYTLDEESRARIKTRLFTIR (SEQ ID NO:
27)

SEQ ID No 28
PA Position 166 to 200
ESRARIKTRLFTIRQEMASRGLWDSFRQSERGEET (SEQ ID NO:
28)

SEQ ID No 29
PA Position 495 to 529
RRKTNLYGFIIKGRSHLRNDTDVVNFVSMEFSLTD (SEQ ID NO:
29)

SEQ ID No 30
PA Position 642 to 676
AKSVFNSLYASPQLEGFSAESRKLLLIVQALRDNL (SEQ ID NO:
30)
```

SEQ ID No 31
PA Position 173 to 207
PRRSGAAGAAVKGVGTMVMELIRMIKRGINDRNFW (SEQ ID NO: 31)

SEQ ID No 32
NP Position 240 to 274
DQVRESRNPGNAEIEDLIFLARSALILRGSVAHKS (SEQ ID NO: 32)

SEQ ID No 33
M1 Position 002 to 026
SLLTEVETYVLSIIPSGPLKAEIAQRLEDVFAGKN (SEQ ID NO: 33)

SEQ ID No 34
M1 Position 023 to 057
EIAQRLEDVFAGKNTDLEALMEWLKTRPILSPLTK (SEQ ID NO: 34)

SEQ ID No 35
M1 Position 038 to 072
DLEALMEWLKTRPILSPLTKGILGFVFTLTVPSER (SEQ ID NO: 35)

SEQ ID No 36
M1 Position 055 to 089
LTKGILGFVFTLTVPSERGLQRRRFVQNALNGNGD (SEQ ID NO: 36)

SEQ ID No 37
M1 Position 166 to 200
ATTTNPLIRHENRMVLASTTAKAMEQMAGSSEQAA (SEQ ID NO: 37)

SEQ ID No 38
NS1 Position 128 to 162
IILKANFSVIFDRLETLILLRAFTEEGAIVGEISP (SEQ ID NO: 38)

SEQ ID No 39
NS2 Position 026 to 060
EDLNGMITQFESLKLYRDSLGEAVMRMGDLHSLQN (SEQ ID NO: 39)

The following sequences were selected from Influenza B consensus sequences. The influenza virus protein and the position of the peptide within that protein are specified. Protein sequences were collected from the Influenza virus resource web site, at ncbi.nlm.nih.gov/genomes/F -continued NP Position 308 to 342 SEQ ID No 61
IADIEDLTLLARSMVVVRPSVASKVVLPISIYAKI (SEQ ID NO: 61)

NP Position 338 to 372 SEQ ID No 62
IYAKIPQLGFNVEEYSMVGYEAMALYNMATPVSIL (SEQ ID NO: 62)

NP Position 418 to 452 SEQ ID No 63
GFHVPAKEQVEGMGAALMSIKLQFWAPMTRSGGNE (SEQ ID NO: 63)

M1 Position 166 to 300 SEQ ID No 64
ARSSVPGVRREMQMVSAMNTAKTMNGMGKGEDVQK (SEQ ID NO: 64)

M1 Position 209 to 237 SEQ ID No 65
IGVLRSLGASQKNGEGIAKDVMEVLKQSS (SEQ ID NO: 65)

Candidate peptides for inclusion into a prophylactic or therapeutic vaccine for influenza may be peptides from any of the viral proteins haemagglutinin, neuraminidase, matrix (M1) protein, M2, nucleoprotein (NP), PA, PB1, PB2, NS1 or NS2 in any such combination.

Synthesis of Fluoropeptides and Native Peptides (Unmodified Peptides)

Eight native peptides and 8 fluoropeptides (selected from the peptide list contained herein; SEQ ID No 1 through 65) were obtained by solid phase peptide synthesis (SPPS). All peptides were synthesized on Rink amide PEG resin by using standard 9-fluorenyhnethoxycarbonyl (Fmoc) chemistry. The peptide chain was assembled on resin by repetitive removal of the Fmoc protecting group by treating with 20% piperidine/N,N-Dimethylformamide for 30 minutes and coupling of protected amino acid by using 1,3-diisopropylcarbodiimide/1-hydroxy-benzotriazole/N-methylmorpholine for 120 minutes. Ninhydrin test was performed after each coupling to check the coupling efficiency. After the addition of the N-terminal Lysinyl residue, the resin blocks were split to allow (1) on the first half of the resin, the incorporation of the 2H,2H,3H,3H-Perfluoroundecanoic acid fluorocarbon chain ($C_8F_{17}(CH_2)_2COOH$) on the Epsilon-chain of the N-terminal lysine to derive the fluoropeptide and (2) on the second half of the resin, the acetylation of the Epsilon-chain of the N-terminal lysine to derive the native peptide. Resins were washed and dried, then treated with reagent K for cleavage and removal of the side chain protecting groups. Crude peptides were precipitated from cold ether and collected by filtration. Purity was assessed by RP-HPLC and was superior to 92% for all peptides. Freeze-dried fluoropeptides were prepared under nitrogen and stored at −20° C. Stability of the fluoropeptides under storage conditions have been confirmed by RP-HPLC and LC-MS over 6 months.

Vaccine Dose Preparation

Eight freeze-dried fluoropeptides (fluoropeptide 1, fluoropeptide 2, fluoropeptide 3, fluoropeptide 4, fluoropeptide 5, fluoropeptide 6, fluoropeptide 7 & fluoropeptide 8) or eight freeze-dried equivalent native peptides (peptide 1, peptide 2, peptide 3, peptide 4, peptide 5, peptide 6, peptide 7 & peptide 8) were formulated to create an isomolar formulation yielding a broadly neutral pH for parenteral delivery.

The sequences of the influenza peptide portions of the constructs were as follows (shown with an $NH_2$ cap on the carboxy terminus):

Fluoropeptide 1
(SEQ ID NO: 1)
HMAIIKKYTSGRQEKNPSLRMKWMMAMKYPITADK-NH2

Fluoropeptide 2
(SEQ ID NO: 4)
VAYMLERELVRKTRFLPVAGGTSSVYIEVLHLTQG-NH2

Fluoropeptide 3
(SEQ ID NO: 17)
YITRNQPEWFRNVLSIAPIMFSNKMARLGKGYMFE-NH2

Fluoropeptide 4
(SEQ ID NO: 18)
APIMFSNKMARLGKGYMFESKXMKLRTQIPAEMLA-NH2

Fluoropeptide 5
(SEQ ID NO: 19)
SPGMMMGMFNMLSTVLGVSILNLGQKKYTKTTY-NH2

Fluoropeptide 6
(SEQ ID NO: 20)
KKKSYINKTGTFEFTSFFYRYGFVANFSMELPSFG-NH2

Fluoropeptide 7
(SEQ ID NO: 32)
DQVRESRNPGNAEIEDLIFLARSALILRGSVAHKS-NH2

Fluoropeptide 8
(SEQ ID NO: 35)
DLEALMEWLKTRPILSPLTKGILGFVFTLTVPSER-NH2

Animals and Immunization

Female, 6-8 weeks of age, BALB/c or CB6F1 (BALB/c×C57BL/6J) mice were purchased from Charles River (UK) &/or Harlan (UK). Injections were performed subcutaneously using 1 ml syringe and 22-G needle. Immunizations were performed so that mice received either a single immunization (prime) or two immunizations (prime/boost). Immunizations were performed with a 14 day interval between each injection.

Figure 2:
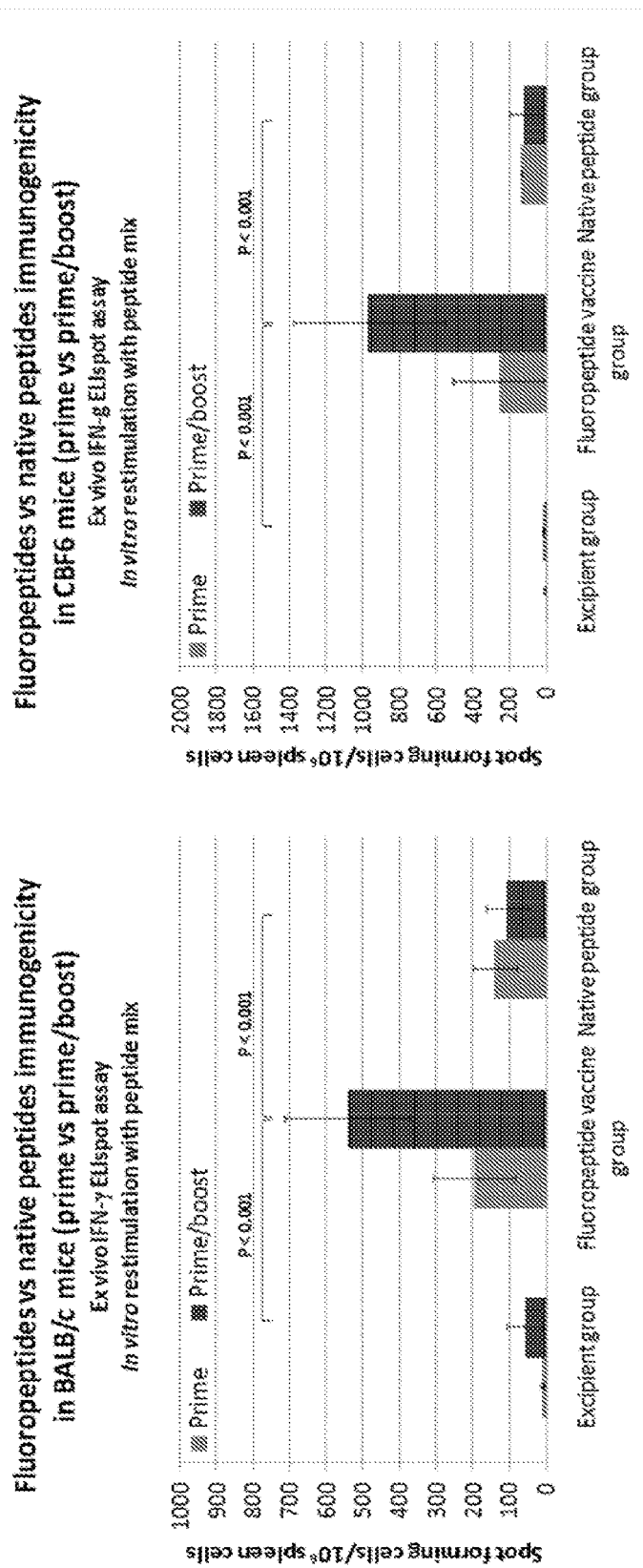
Figure 3:
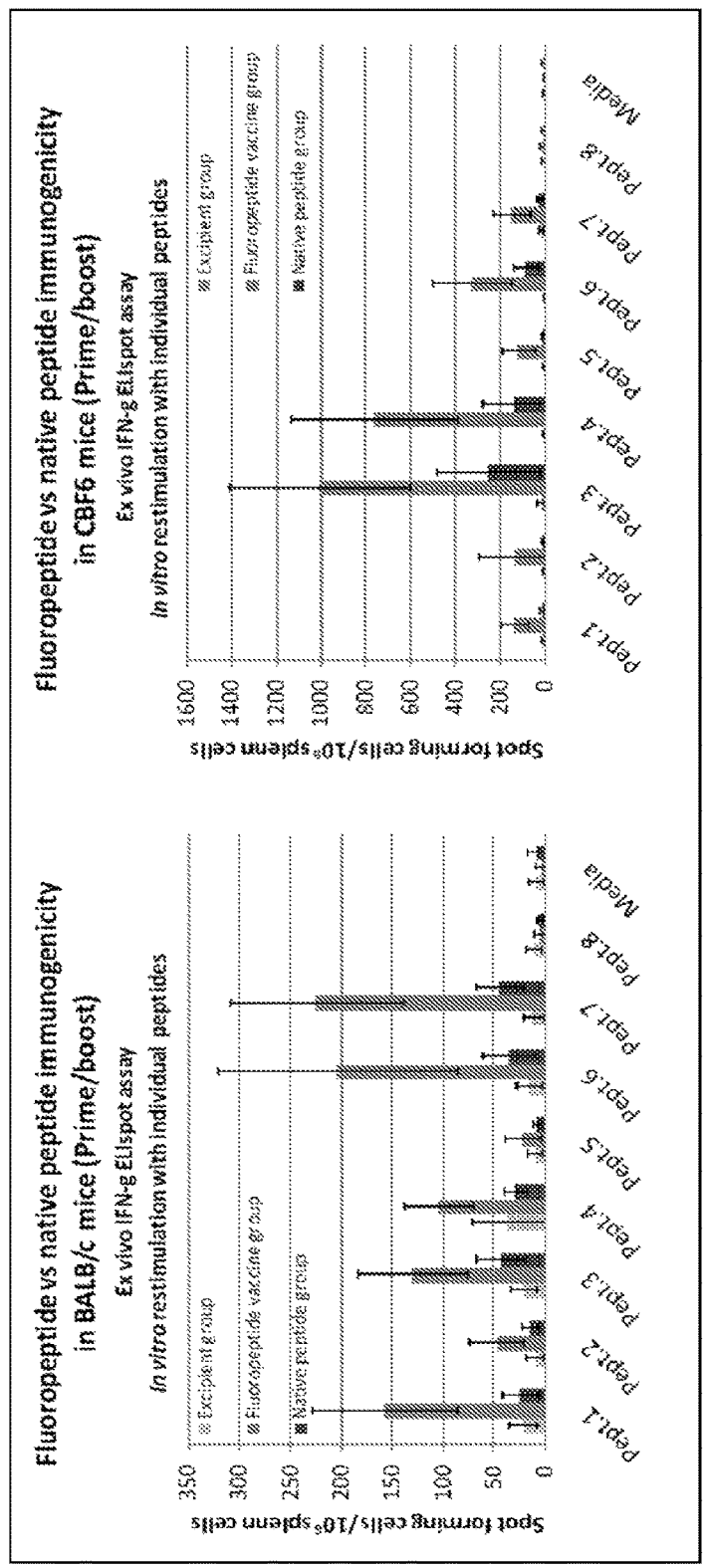

Fluoropeptide Vaccine is Strongly Immunogenic and is Superior to Native Peptides in Both BALB/c and CB6F1 Mice The immunogenicity of the fluoropeptide vaccine (mixture of 8 fluoropeptides as above) was compared to the native peptide equivalent (mixture of 8 unmodified peptides—called native peptides as above) in BALB/c and CB6F1 mice. The study also compared the immunogenicity of both formulations using a prime or prime-boost regimen. Both formulations were injected subcutaneously without adjuvant in BALB/c and CBF6 mice. Mice were immunized with a fluoropeptide vaccine dose containing 1 nmol/fluoropeptide (8 nmol total for eight fluoropeptides) or the native peptide vaccine equivalent at 1 nmol/peptide (8 nmol total for eight native peptides). Neither vaccine preparation contained any adjuvant. 10 days after the final immunization, spleen cells were restimulated with each individual native peptide at 10 µg/ml and assessed using an IFN-γ ELISpot assay. According to ex vivo IFN-γ ELISpot assays (FIGS. 1 & 2), the immunogenicity of the fluoropeptide vaccine was superior to both the excipient alone and the native peptide vaccine equivalent after a prime-boost immunization regimen (P<0.001). The results also demonstrated a strong increase in the number of spot forming cells using a prime-boost regimen compared to a single immunization for the fluoropeptide vaccine group only (FIGS. 1 & 2). These results demonstrate the self-adjuvanticity property of the fluorocarbon chain linked to a peptide sequences.

Fluoropeptide Vaccine Induces a Robust Multiepitopic T Cell Response in Both BALB/c and CB6F1 Mice The immunogenicity of the fluoropeptide vaccine (mixture of 8 fluoropeptides as above) was compared to its native peptide equivalent (mixture of 8 unmodified peptides—referred to as 'native peptides' as above) in BALB/c and CB6F1 mice. The study also compared the immunogenicity of both formulations on a prime and prime-boost regimen. Both formulations were injected subcutaneously without adjuvant in BALB/c and CB6F1 mice. Mice were immunized with a fluoropeptide vaccine dose containing 1 nmol/fluoropeptide (8 nmol total for eight fluoropeptides), the native peptide vaccine equivalent at 1 nmol/peptide (8 nmol total for eight native peptides). Neither vaccine preparation contained any adjuvant. The control group consisted of mice immunized with excipient alone. 10 days after immunization, spleen cells were restimulated by each individual native peptide at 10 µg/ml and assessed using IFN-γ ELISpot assay. The fluoropeptide vaccine induce peptide-specific responses directed against 5 out of 8 peptides in BALB/c mice and 7 out of 8 peptides in CB6F1 mice which is superior to the response induced by the vaccine equivalent (unmodified peptides). This demonstrates that vaccination with fluoropeptides can induce an immunological response that is both qualitatively and quantitatively superior to that of its native peptide equivalent.

The Fluoropeptide Vaccine Induces a Th1 Cytokine Profile Depending Upon the Murine Strain Tested The immunogenicity of the fluoropeptide vaccine (mixture of 8 fluoropeptides as above) was compared to the native peptide equivalent (mixture of 8 unmodified peptides as above) in BALB/c and CB6F1 mice. Formulations were injected subcutaneously without adjuvant in BALB/c and CB6F1 mice. Mice were immunized with a fluoropeptide vaccine dose containing 1 nmol/fluoropeptide (8 nmol total for eight fluoropeptides), the native peptide vaccine equivalent at 1 nmol/peptide (8 nmol total for eight native peptides). Neither vaccine preparation contained any adjuvant. 10 days after the last immunization, spleen cells were restimulated with a mixture of 8 native peptides at 1 µg/ml per peptide. After 48 hours stimulation culture supernatants were assessed for cytokines by means of a multiplexed bead assay (CBA). Results demonstrate the cytokine profile in CBF6 mice is dominated by the production of IFN-γ and significant production of TNF-α highlighting a Th1 profile (FIG. 4). This Th1-dominated cytokine profile was more pronounced compared to BALB/c mice due to a lower intensity of these Th1 responses compared to CB6F1 mice (as also observed by IFN-γ ELISpot—refer to FIGS. 1 & 2) and increases in Th2 cytokines. Nevertheless, an enhanced Th1 response was observed in BALB/c mice immunized with fluoropeptides compared to its native peptide equivalent.

The Fluoropeptide Vaccine Stimulates Both Peptide-Specific CD4+ and CD8+ T Cells Producing IFN-γ

Intracellular cytokine staining for IFN-γ was used to provide information about the frequency of peptide-specific CD4+ and CD8+ T cells producing IFN-γ. Mice were immunized with the fluoropeptide vaccine (mixture of 8 fluoropeptides as above) and CD4+ or CD8+ splenocytes were assessed for intracellular cytokine staining by flow cytometry after a short stimulation period with a mixture of 8 native peptides (vaccine). The results demonstrate that immunization of mice with the fluoropeptide vaccine was able to elicit both peptide-specific CD4+ and CD8+ T cells producing IFN-γ at a frequency of 0.5-2.6% (FIG. 5). This validates that fluoropeptides engage both MHC class I & II antigen processing peptides if the peptides contain relevant MHC class I & II epitopes.

Example 2. Immune Responses Elicited by Fluoropeptide Vaccination are Boosted by Combination with Adjuvant Immunogenicity of the fluoropeptide vaccine (mixture of 8 fluoropeptides as above) was compared with immunogenicity of the fluoropeptide vaccine in the presence of an adjuvant, Freund's complete adjuvant (FCA). Fluoropeptide vaccine (1 nmol/peptide) or fluoropeptide vaccine (1 nmol/peptide) emulsified in CFA was used to immunize BALB/c mice. 10 days after the immunization, splenocytes were stimulated with individual peptides at 10 µg/ml. 48 hours later culture supernatants were collected and tested for cytokines using a multiplex cytokine assay (CBA). Results show that using an CFA as an additional adjuvant can significantly boost Th1 cytokine production (IFN-γ and IL-2) without effecting the production of Th2 cytokines (IL-4, IL-5) (FIG. 6). Therefore Th1 responses induced by fluoropeptide vaccination are preferentially boosted by combination with adjuvant during immunization.

Both Subcutaneous and Intradermal Routes of Fluoropeptide Vaccine Administration can Induce Immune Responses Immunogenicity of the fluoropeptide vaccine (mixture of 8 fluoropeptides as above) was compared using either intradermal or subcutaneous routes of administration in BALB/c mice. 10 days after the immunization, splenocytes were stimulated with individual peptides at 10 µg/ml and assessed for ex vivo IFN-γ production by means of ELISPOT. Results show that both subcutaneous and intradermal routes of fluoropeptide administration are suitable to induce robust antigen-specific responses (FIG. 7).

INCORPORATION BY REFERENCE

The entire disclosure of each of the publications and patent documents referred to herein is incorporated by reference in its entirety for all purposes to the same extent as if each individual publication or patent document were so individually denoted.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A vector-antigen construct comprising:
an antigenic influenza peptide sequence covalently attached to a vector, wherein the vector is of structure $C_mX_n$—$C_yH_x$-(Sp)-R, wherein m=3 to 30, n<=2m+1, y=0 to 15, x<=2y, (m+y)=3 to 30, Sp is an optional chemical spacer moiety, R is the antigenic influenza peptide and X is selected from a fluorine, chlorine, bromine or iodine, and wherein the antigenic influenza peptide is up to 40 amino acids in length and comprises any one of SEQ ID NOs: 1 to 65.

2. The vector-antigen construct of claim 1, wherein the antigenic influenza peptide comprises an amino acid sequence of any one of SEQ ID NOs: 1, 4, 17, 18, 32 or 35.

3. The vector-antigen construct of claim 1, wherein the vector is of structure $C_mF_n$—$C_yH_x$-(Sp)-R, wherein m=3 to 30, n<=2m+1, y=0 to 15, x<=2y, (m+y)=3 to 30, Sp is an optional chemical spacer moiety and R is the antigenic influenza peptide.

4. The vector-antigen construct of claim 1, wherein the vector comprises structure $F_3C$—$CF_2$—$CF_2$—$CF_2$—$CF_2$—$CF_2$—$CF_2$—Sp—R where Sp is an optional chemical spacer moiety and R is the antigenic influenza peptide.

5. A pharmaceutical composition for intracellular delivery of an antigen, the composition comprising an antigenic influenza peptide sequence covalently attached to a vector, wherein the vector is of structure $C_mX_n$—$C_yH_x$-(Sp)-R, wherein m=3 to 30, n<=2m+1, y=0 to 15, x<=2y, (m+y)=3 to 30, Sp is an optional chemical spacer moiety, R is the antigenic influenza peptide and X is selected from a fluorine, chlorine, bromine or iodine, and wherein the antigenic influenza peptide is up to 40 amino acids in length and comprises any one of SEQ ID NOs: 1 to 65.

6. The composition of claim 5, wherein the vector is of structure $C_mF_n$—$C_yH_x$-(Sp)-R, wherein m=3 to 30, n<=2m+1, y=0 to 15, x<=2y, (m+y)=3 to 30, Sp is an optional chemical spacer moiety and R is the antigenic influenza peptide.

7. The composition of claim 5, wherein the vector comprises structure $F_3C$—$CF_2$—$CF_2$—$CF_2$—$CF_2$—$CF_2$—$CF_2$—Sp—R where Sp is an optional chemical spacer moiety and R is the antigenic influenza peptide.

8. The composition of claim 5, wherein the composition comprises from 2 to 20 of the antigenic influenza peptide sequences each covalently attached to a vector.

9. The composition of claim 5, wherein the composition comprises 5, 6, 7, or 8 of the antigenic influenza peptide sequences each covalently attached to a vector.

10. The composition of claim 5, further comprising one or more pharmaceutically acceptable carriers, excipients, diluents or adjuvants.

11. The composition of claim 5, formulated for parenteral, oral, ocular, rectal, nasal, transdermal, topical or vaginal administration.

12. The composition of claim 5, wherein the composition is in a form of a liquid, emulsion, solid, aerosol or gas.

13. A method of stimulating an immune response, comprising administering the composition of claim 5 to an animal.

14. The method of claim 13, wherein the animal is a mammal, a bird or a human.

15. A method of preparing a prophylactic or therapeutic pharmaceutical composition comprising combining the composition of claim 5, with one or more pharmaceutically acceptable carriers, excipients, diluents or adjuvants.

* * * * *